US008897876B2

(12) United States Patent
Sundaramurthy et al.

(10) Patent No.: US 8,897,876 B2
(45) Date of Patent: Nov. 25, 2014

(54) SYSTEMS AND METHODS FOR MAKING AND USING CONNECTORS FOR ELECTRICAL STIMULATION SYSTEMS

(75) Inventors: Priya Sundaramurthy, Fremont, CA (US); Aditya Vasudeo Pandit, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 196 days.

(21) Appl. No.: 13/226,813

(22) Filed: Sep. 7, 2011

(65) Prior Publication Data

US 2012/0071937 A1 Mar. 22, 2012

Related U.S. Application Data

(60) Provisional application No. 61/385,298, filed on Sep. 22, 2010.

(51) Int. Cl.
*A61N 1/372* (2006.01)
*H01R 24/58* (2011.01)
*A61N 1/375* (2006.01)

(52) U.S. Cl.
CPC .............. *H01R 24/58* (2013.01); *A61N 1/3752* (2013.01); *H01R 2201/12* (2013.01)
USPC .................................. 607/37; 607/36; 607/38

(58) Field of Classification Search
CPC .................................................... A61N 1/3752
USPC ..................................................... 607/36–38
See application file for complete search history.

(56) References Cited

U.S. PATENT DOCUMENTS

| 3,951,154 | A | * | 4/1976 | Hartlaub | 607/37 |
|---|---|---|---|---|---|
| 3,990,727 | A | | 11/1976 | Gallagher | |
| 4,712,557 | A | * | 12/1987 | Harris | 607/37 |
| 5,968,082 | A | * | 10/1999 | Heil | 607/37 |
| 6,181,969 | B1 | | 1/2001 | Gord | |
| 6,430,442 | B1 | * | 8/2002 | Peters et al. | 607/37 |
| 6,516,227 | B1 | | 2/2003 | Meadows et al. | |
| 6,609,029 | B1 | | 8/2003 | Mann et al. | |
| 6,609,032 | B1 | | 8/2003 | Woods et al. | |
| 6,671,534 | B2 | * | 12/2003 | Putz | 600/378 |
| 6,741,892 | B1 | | 5/2004 | Meadows et al. | |
| 7,069,081 | B2 | | 6/2006 | Biggs et al. | |
| 7,191,009 | B2 | * | 3/2007 | Laske et al. | 607/37 |

(Continued)

FOREIGN PATENT DOCUMENTS

EP 1625875 A1 2/2006

*Primary Examiner* — Joseph Stoklosa
(74) *Attorney, Agent, or Firm* — Lowe Graham Jones PLLC; Bruce E. Black

(57) ABSTRACT

A connector for an implantable medical device includes an elongated connector housing having a first end, a second end, a length, and an outer surface. The connector housing defines a port at the second end of the connector housing that extends along the length toward the first end. The port is configured and arranged for receiving a proximal end of lead or lead extension. Connector contacts disposed in the connector housing are configured and arranged for coupling to terminals disposed on the lead or lead extension when the lead or lead extension is received by the port. At least one window is defined along the outer surface of the connector housing. The at least one window is configured and arranged for viewing at least a portion of the lead or lead extension when the lead or lead extension is received by the port.

9 Claims, 24 Drawing Sheets

(56) References Cited

U.S. PATENT DOCUMENTS

| | | |
|---|---|---|
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 2005/0165465 A1 | 7/2005 | Pianca et al. |
| 2007/0150036 A1 | 6/2007 | Anderson |
| 2007/0219595 A1 | 9/2007 | He |
| 2008/0071320 A1 | 3/2008 | Brase |

* cited by examiner

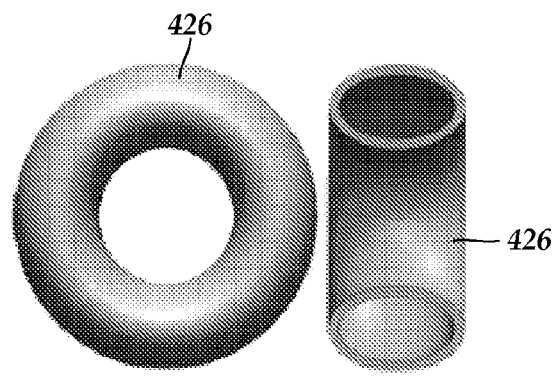
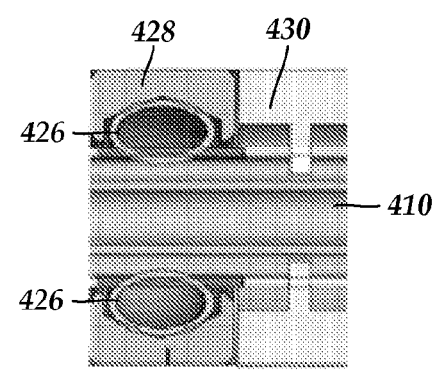
Fig. 7A         Fig. 7B
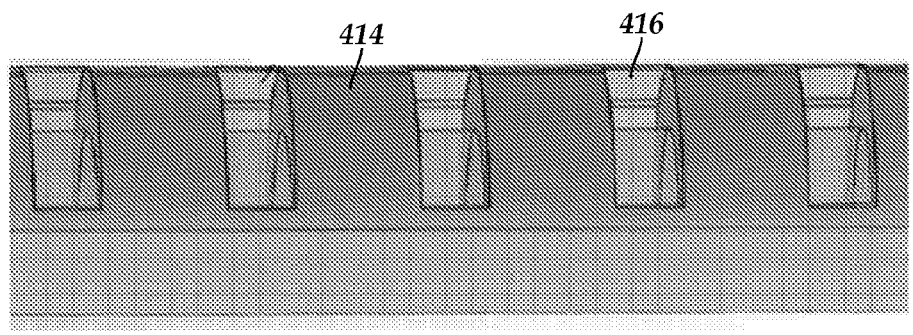
Fig. 8A

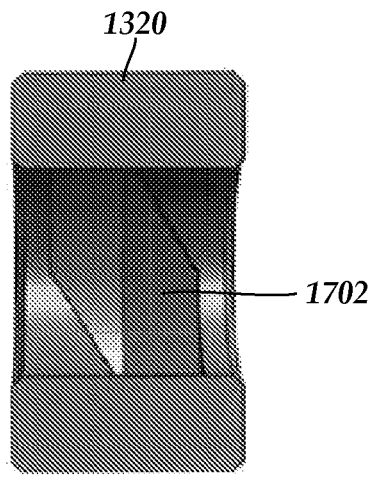
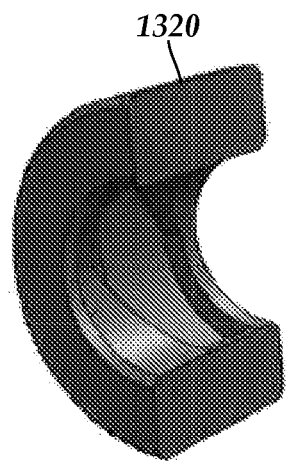
Fig. 17A          Fig. 17B
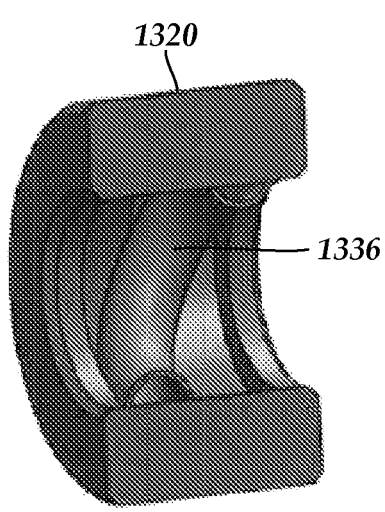
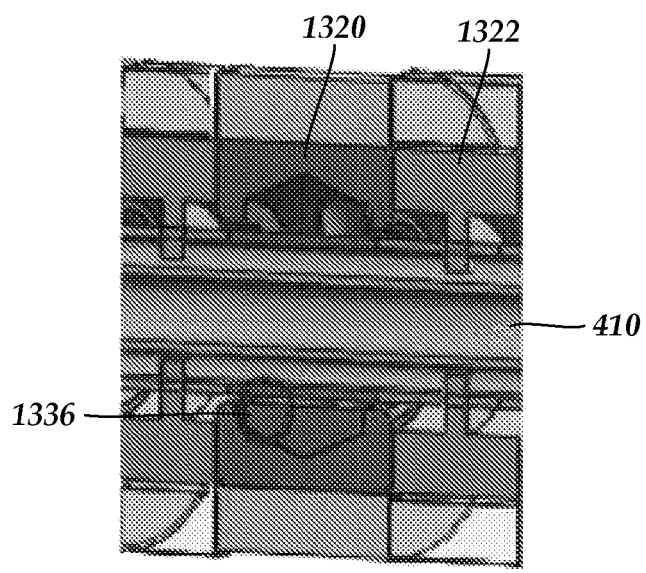
Fig. 18A          Fig. 18B

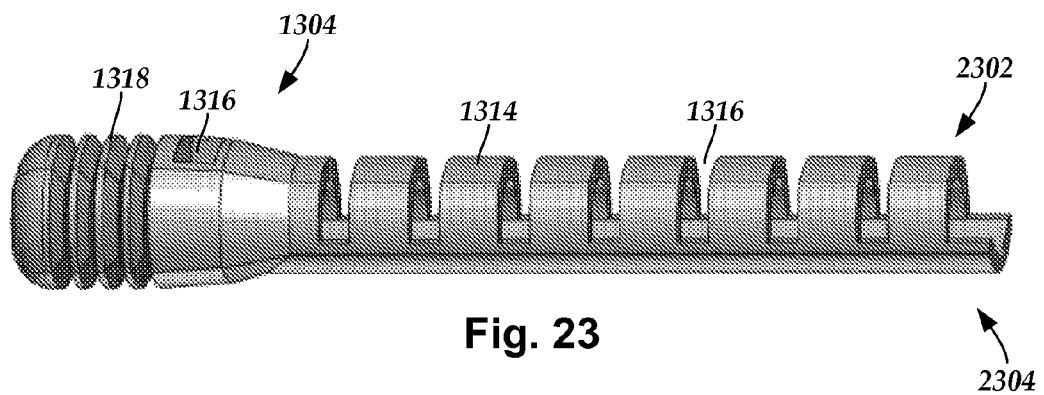
Fig. 23
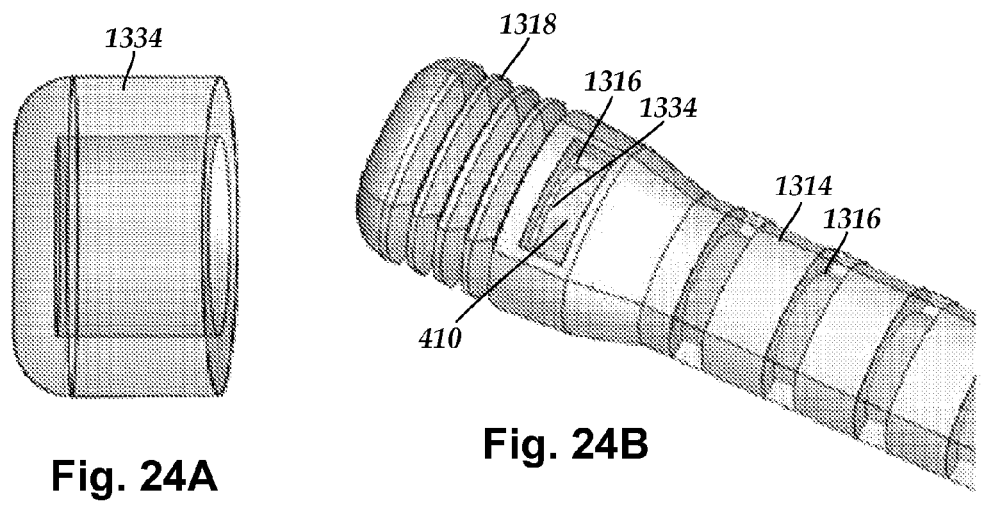
Fig. 24A
Fig. 24B

SYSTEMS AND METHODS FOR MAKING AND USING CONNECTORS FOR ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/385,298 filed on Sep. 22, 2010, which is incorporated herein by reference.

FIELD

The present invention is directed to the area of implantable electrical stimulation systems and methods of making and using the systems. The present invention is also directed to connectors for receiving leads or lead extensions, as well as methods of making and using the connectors, leads, lead extensions, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for an implantable medical device includes an elongated connector housing having a first end, a second end, a length, and an outer surface. The connector housing defines a port at the second end of the connector housing that extends along at least a portion of the length of the connector housing. The port is configured and arranged for receiving a proximal end of a lead or lead extension. A plurality of connector contacts are disposed in the connector housing. The connector contacts are configured and arranged for coupling to terminals disposed on the proximal end of the lead or lead extension when the proximal end of the lead or lead extension is received by the port. At least one window is defined along the outer surface of the connector housing. The at least one window is configured and arranged for viewing at least a portion of the lead or lead extension when the lead or lead extension is received by the port.

In another embodiment, a connector for an implantable medical device includes an elongated connector housing having a first end, a second end, a length, and an outer surface. The connector housing defines a port at the second end of the connector housing that extends along at least a portion of the length of the connector housing. The port is configured and arranged for receiving a proximal end of a lead or lead extension. A plurality of connector contacts are disposed in the connector housing. The connector contacts are configured and arranged for coupling to terminals disposed on the proximal end of the lead or lead extension when the proximal end of the lead or lead extension is received by the port. A retaining element is configured and arranged for retaining the lead or lead extension when the lead or lead extension is received by the port. The retaining element includes a pin vice.

In yet another embodiment, a connector for an implantable medical device includes an elongated connector housing having a first end, a second end, a length, and an outer surface. The connector housing defines a port at the second end of the connector housing that extends along at least a portion of the length of the connector housing. The port is configured and arranged for receiving a proximal end of a lead or lead extension. A plurality of connector contacts are disposed in the connector housing. The connector contacts are configured and arranged for coupling to terminals disposed on the proximal end of the lead or lead extension when the proximal end of the lead or lead extension is received by the port. At least one strain relief arrangement is disposed along at least a portion of the connector housing. The at least one strain relief arrangement includes a plurality of interconnected pleats configured and arranged to expand and contract along the length of the connector housing to absorb strain placed on the connector.

In another embodiment, a connector for an implantable medical device includes an elongated connector housing having a first end, a second end, a length, and an outer surface. The connector housing defines a port at the second end of the connector housing that extends along at least a portion of the length of the connector housing. The port is configured and arranged for receiving a proximal end of a lead or lead extension. A plurality of connector contacts are disposed in the connector housing. The connector contacts are configured and arranged for coupling to terminals disposed on the proximal end of the lead or lead extension when the proximal end of the lead or lead extension is received by the port. An end stop is disposed at a proximal end of the port. The end stop includes a feedback mechanism for providing audible feedback to a user when, during insertion of the proximal end of the lead or lead extension into the port, the proximal end of the lead or lead extension contacts the end stop.

In yet another embodiment, a connector for an implantable medical device includes an elongated connector housing having a first end, a second end, a length, and an outer surface. The connector housing defines a port at the second end of the connector housing that extends along at least a portion of the length of the connector housing. The port is configured and arranged for receiving a proximal end of a lead or lead extension. A plurality of coupleable members are coupled together along the length of the connector housing. The plurality of coupleable members include a plurality of first coupleable members each having at least one contact. The contacts are configured and arranged to couple to terminals of the proximal end of the lead of lead extension when the proximal end of the lead or lead extension is received by the port. A plurality of second coupleable members include non-conductive spacers. At least one of the plurality of second coupleable members is disposed between adjacent first coupleable members. Each of the plurality of first and the second coupleable members defines a port aperture configured and arranged to form a portion of a length of the port when the coupleable members are coupled together. The first and the second coupleable members are configured and arranged to retain the lead or lead extension when the lead or lead extension is received by the port by forming an interference fit between walls of the port and an outer surface of the lead or lead extension.

In another embodiment, a connector for an implantable medical device includes two body portions each having a first end, a second end, and a length. The two body portions are coupled together along the lengths of the body portions by at least one hinge coupled to both body portions and extending along a fulcrum. The hinge enables the two body portions to pivot the connector open or closed. The body portions each include an inner pocket. The inner pockets collectively form a contact housing configured and arranged for receiving a proximal end of a lead or lead extension. A plurality of connector contacts are disposed in the contact housing. The connector contacts are configured and arranged to couple to terminals of the proximal end of the lead of lead extension when the proximal end of the lead or lead extension is received by the contact housing. A locking mechanism is configured and arranged for retaining the proximal end of the lead or lead extension within the contact housing. The locking mechanism includes at least one pin disposed on one of the two body portions and at least one retaining aperture disposed on the other of the two body portions. The at least one retaining aperture is configured and arranged to receive the at least one pin when the body portions are closed.

In yet another embodiment, a lead extension for an implantable medical device includes a lead extension body having a proximal end and a distal end. A plurality of terminals are disposed at the proximal end of the lead extension body. An elongated connector housing is coupled to the distal end of the lead extension body, the connector housing has a first end, a second end, a length, and an outer surface. The connector housing defines a port at the second end of the connector housing that extends along at least a portion of the length of the connector housing. The port is configured and arranged for receiving a proximal end of a lead or lead extension. A plurality of connector contacts are disposed in the connector housing. At least one window is defined along the outer surface of the connector housing. The at least one window is configured and arranged for viewing at least a portion of the lead or lead extension when the lead or lead extension is received by the port. A plurality of conductors each electrically couple at least one of the connector contacts to at least one of the terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is a schematic side view and a longitudinal cross-sectional view of one embodiment of a connector contact suitable for use with the connector of FIG. 4A, according to the invention;

FIG. 7B is a schematic longitudinal cross-sectional view of one embodiment of a lead or lead extension inserted into a portion of the connector of FIG. 4A, the portion of the connector including the connector contact of FIG. 7A and an adjacent spacer, according to the invention;

FIG. 8A is a schematic perspective view of one embodiment of a portion of a connector housing suitable for use with the connector of FIG. 4A, the connector housing including an array of apertures, according to the invention;

FIG. 17A is a schematic side view of one embodiment of a partially-cylindrical housing suitable for receiving a diagonally-extending conductive contact within the connector of FIG. 13A, according to the invention;

FIG. 17B is a schematic perspective view of one embodiment of the partially-cylindrical housing of FIG. 17A, according to the invention;

FIG. 18A is a schematic perspective view of one embodiment of a partially-cylindrical, diagonally-extending conductive contact disposed in the partially-cylindrical housing of FIG. 17A, according to the invention;

FIG. 18B is a schematic longitudinal cross-sectional view of one embodiment of a portion of a lead or lead extension inserted into a portion of the connector of FIG. 13A such that the lead or lead extension is in contact with the partially-cylindrical, diagonally-extending conductive contact of FIG. 18A, according to the invention;

FIG. 23 is a schematic side perspective view of one embodiment of a connector housing suitable for use with the connector of FIG. 13A, the connector housing defining an array of apertures, according to the invention;

FIG. 24A is a schematic perspective view of one embodiment of an end stop suitable for use with the connector of FIG. 13A, the end stop including a transparent region, according to the invention;

FIG. 24B is a schematic perspective view of one embodiment of a distal portion of the connector of FIG. 13A, the distal end of the connector including an expandable strain relief arrangement and a window disposed in the connector housing over the end stop of FIG. 24A, according to the invention;

DETAILED DESCRIPTION

The present invention is directed to the area of implantable electrical stimulation systems and methods of making and using the systems. The present invention is also directed to connectors for receiving leads or lead extensions, as well as methods of making and using the connectors, leads, lead extensions, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and U.S. Patent Applications Publication Nos. 2005/0165465; 2007/0150036; 2007/0219595; and 2008/0071320, all of which are incorporated by reference.

Figure 1:
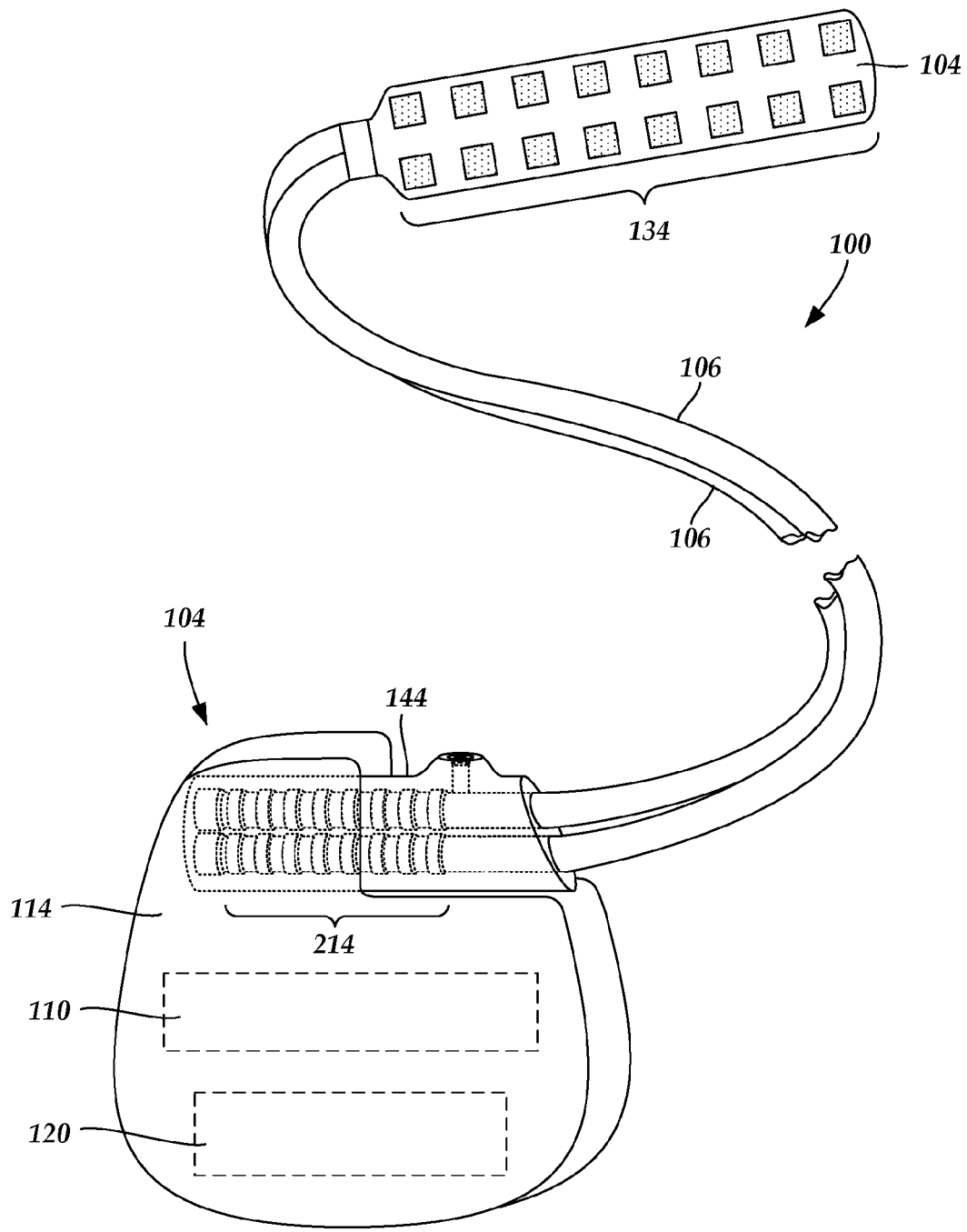
FIG. 1 is a schematic view of one embodiment of an electrical stimulation system, according to the invention.
Figure 2:
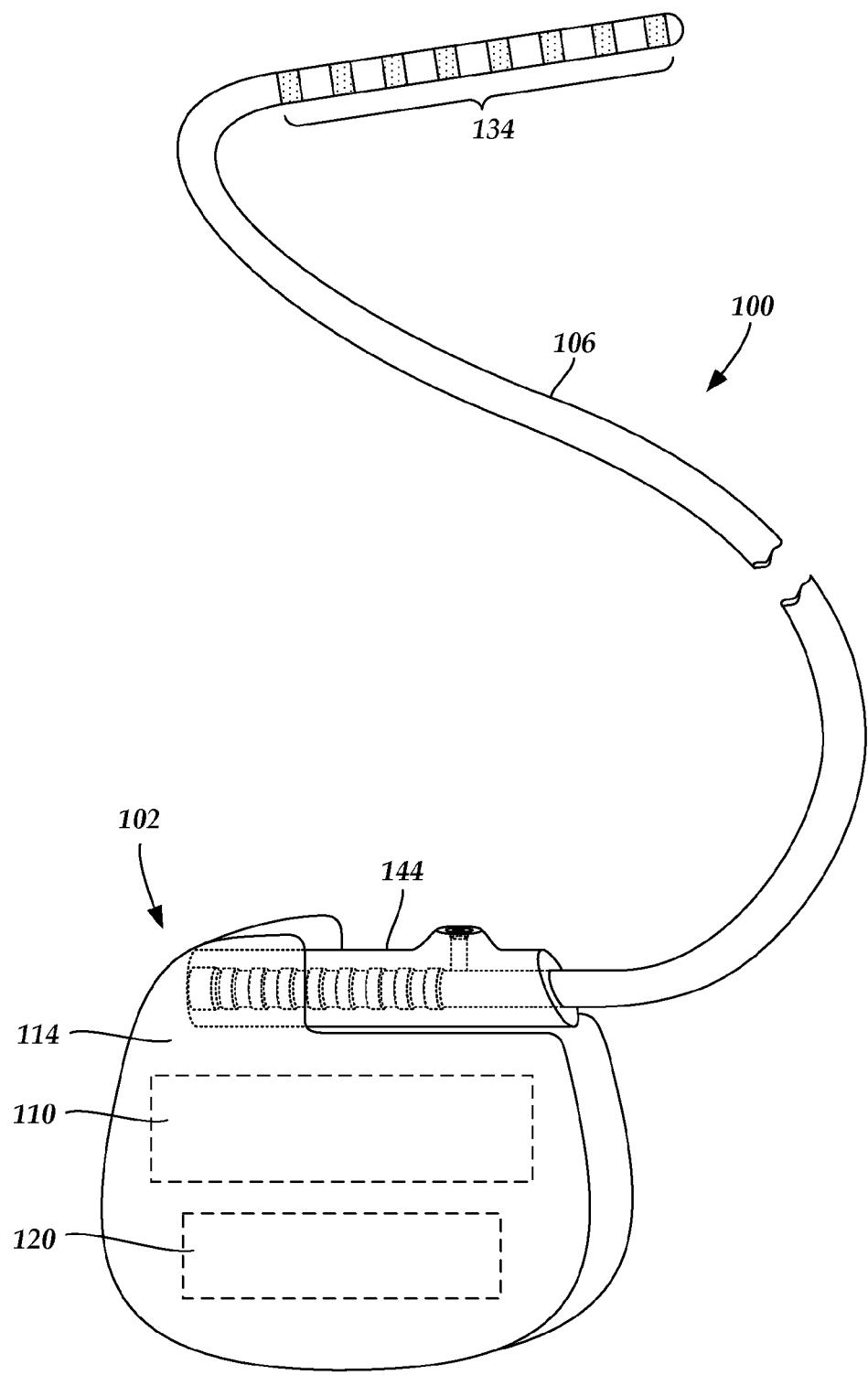
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. In FIG. 1, two lead bodies 106 are shown. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIGS. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A and 336 of FIG. 3B) are typically disposed at the proximal end of the one or more lead bodies 106 for connection to corresponding conductive contacts (e.g., 314 in FIGS. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIGS. 3A and 336 of FIG. 3B) to the electrodes 134. Typically, one or more electrodes 134 are electrically coupled to a terminal (e.g., 310 in FIGS. 3A and 336 of FIG. 3B). In some embodiments, each terminal (e.g., 310 in FIGS. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
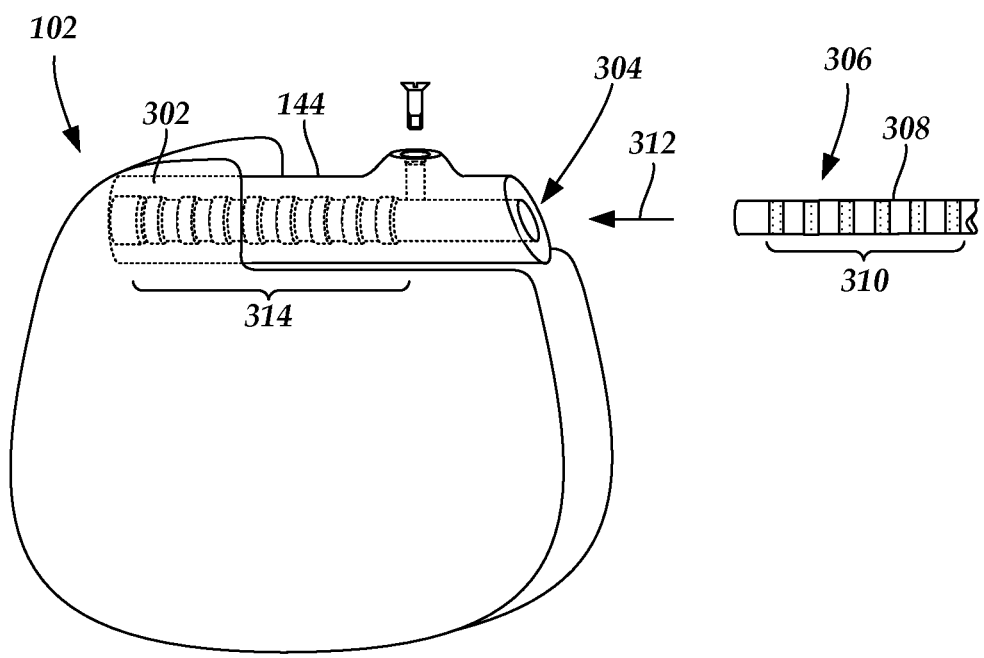
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a contact housing 302. The contact housing 302 defines at least one port 304 into which a proximal end 306 of a lead 308 with terminals 310 can be inserted, as shown by directional arrow 312. The contact housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. Patent Application Publication No. 2008/0071320 A1, which are incorporated by reference.

Figure 3B:
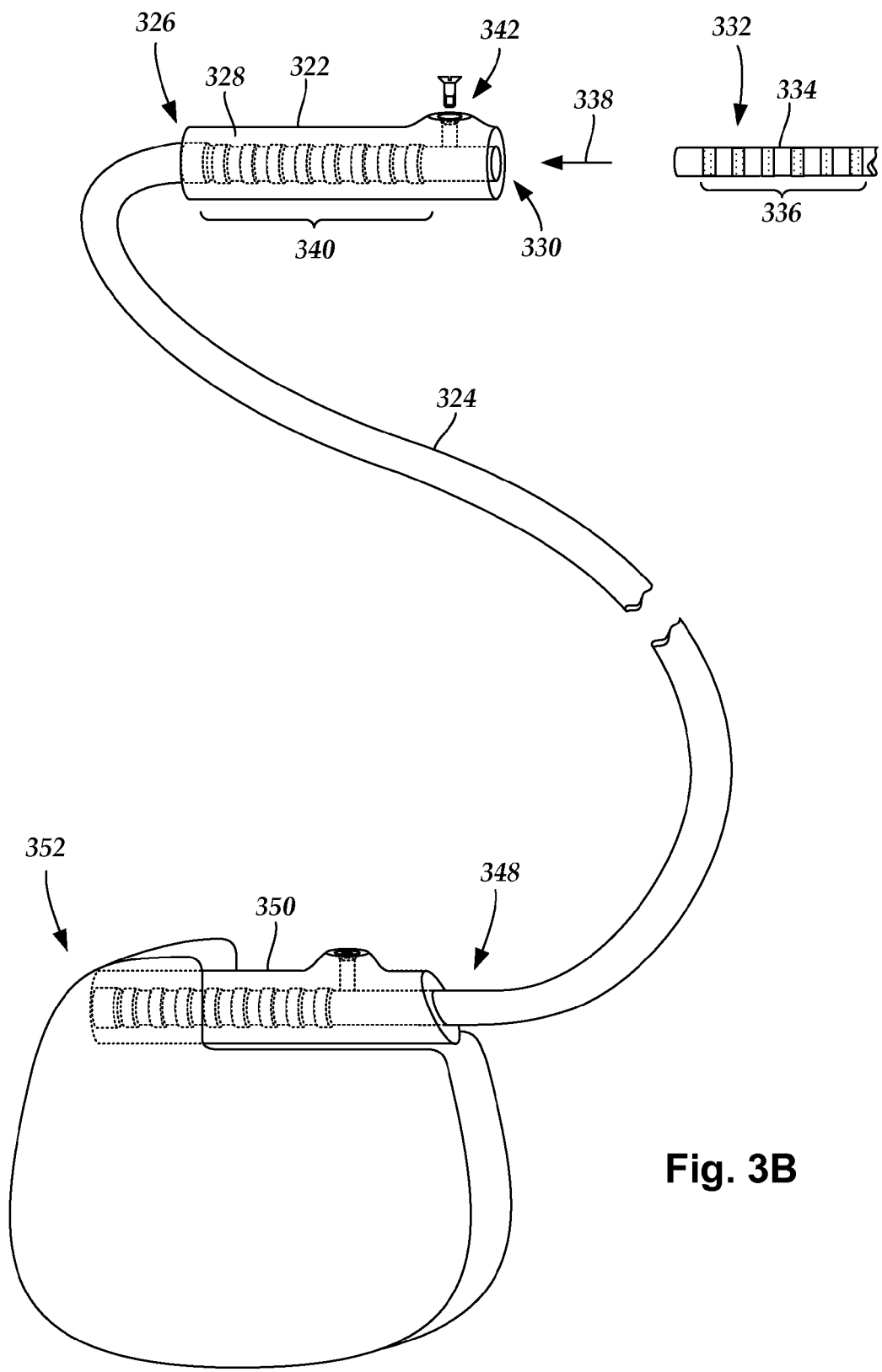
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a contact housing 328. The contact housing 328 defines at least one port 330 into which a proximal end 332 of a lead 334 with terminals 336 can be inserted, as shown by directional arrow 338. The contact housing 328 also includes a plurality of connector contacts 340. When the lead 334 is inserted into the port 330, the connector contacts 340 disposed in the contact housing 328 can be aligned with the terminals 336 on the lead 334 to electrically couple the lead extension 324 to the electrodes (134 of FIG. 1) disposed at a distal end (not shown) of the lead 334. The connector 322 further includes a retaining element 342 configured and arranged to fasten the lead 334 to the connector 322 when the lead 334 is inserted into the at least one port 330.

In at least some embodiments, the proximal end of a lead extension is similarly configured and arranged as a proximal end of a lead. The lead extension 324 may include a plurality of conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Connectors typically have transverse diameters that are larger than a corresponding lead or lead extension to accommodate insertion of one end of the corresponding lead or lead extension into the connector. The larger diameters of connectors can potentially reduce the number of suitable locations for implantation. Additionally, connectors with relatively large diameters may increase patient discomfort during the implantable lifetime of the electrical stimulation system. Decreasing the transverse diameters of connectors may decrease patient discomfort during the implantable lifetime of the electrical stimulation system. Thus, it may be advantageous to form connectors, such as connector 322 of FIG. 3B, with transverse diameters that are not much larger than the transverse diameters of corresponding leads or lead extensions.

At least some conventional connectors include retaining elements, such as retaining element 342 of FIG. 3B, with transverse diameters that are greater than transverse diameters of remaining portions of the contact housing. Thus, it may also be advantageous to reduce the transverse diameters of the retaining elements in comparison to the remaining portion of the contact housing. It may also be advantageous to provide isodiametric connectors, or transverse diameters that remain constant (or nearly constant) along a length of the connectors.

Patient movement may eventually cause a lead or lead extension inserted into a connector to loosen, or even disconnect, from the connector, thereby reducing, or even completely discontinuing, the therapeutic effects of the electrical stimulation system. For example, loosening of the lead or lead extension within the connector may cause terminals of the lead or lead extension to become partially, or even fully, misaligned with connector contacts disposed in the connector. It may, therefore, be advantageous to form a connector such that an inserted lead or lead extension is more likely to remain inserted into the connector despite bending, twisting, and stretching caused by patient movement over time.

When a lead or lead extension is inserted into a conventional connector, there may not be any feedback provided to the medical practitioner for gauging the degree of insertion of the lead or lead extension into the port of the connector. Consequently, a lead or lead extension may be inserted into the connector such that the lead or lead extension appears to be properly inserted, yet terminals of the lead or lead extension are, in fact, not fully contacting conductive contacts of the connector. In such cases, the connector and the lead or lead extension may be more likely to loosen or disconnect from one another over time. It may, therefore, be advantageous to form a connector that enables a medical practitioner to more easily identify when a lead or lead extension is fully inserted into the connector. It may further be advantageous to form a connector that enables a medical practitioner to identify when terminals of a lead or lead extension are aligned with connector contacts of the connector as the lead or lead extension is inserted into the connector. It may also be advantageous to form a connector with connector contacts that increase the likelihood of maintaining contact with terminals of an inserted lead or lead extension, despite small misalignments.

It may also be useful to provide a lead extension with a connector having a smaller transverse diameter than the connector 322 illustrated in FIG. 3B. It may also be useful to provide a lead extension with a connector having a retaining element with a smaller transverse diameter than the retaining element 342 illustrated in FIG. 3B. It may also be useful to provide a lead extension with a contact housing that is isodiametric, or nearly isodiametric. It may further be useful to provide a connector having a strain relief arrangement. It may further be useful to provide a connector that provides feedback to a medical practitioner regarding the relative insertion of a lead or other lead extension into the connector.

Figure 4A:
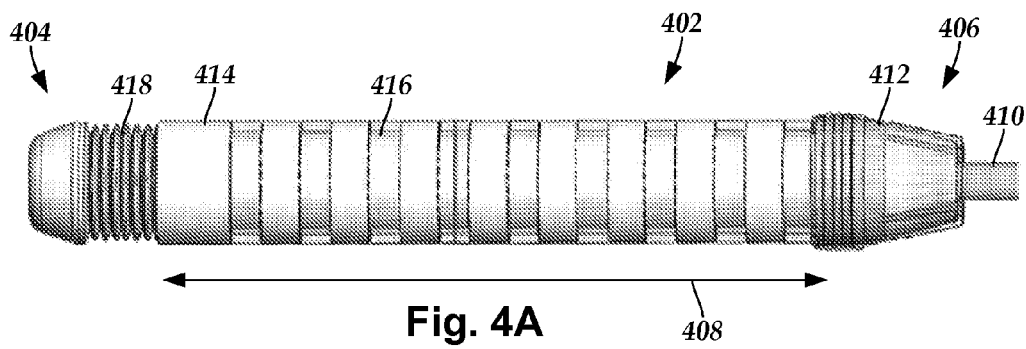
FIG. 4A is a schematic side view of one embodiment of a lead or lead extension inserted into a connector of an electrical stimulation system, according to the invention.
Figure 13A:
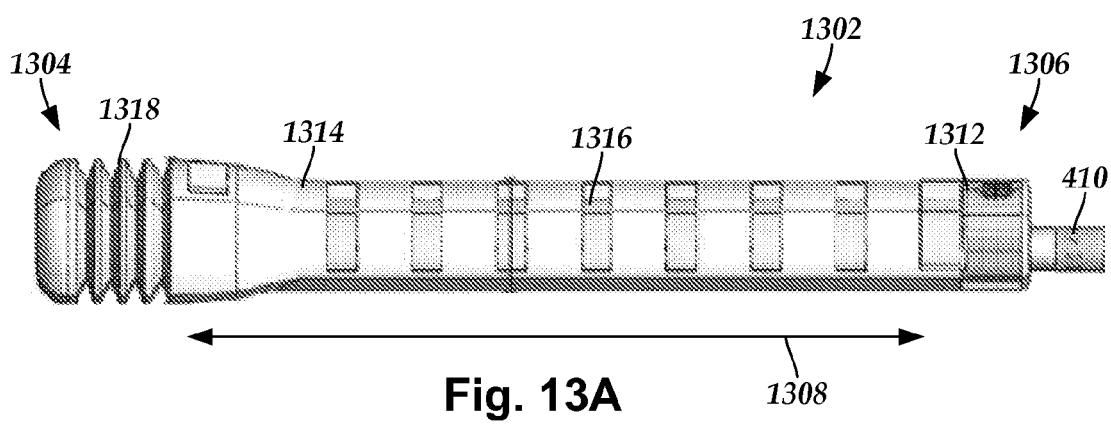
FIG. 13A is a schematic side view of a lead or lead extension inserted into a second embodiment of a connector of an electrical stimulation system, according to the invention.
Figure 25A:
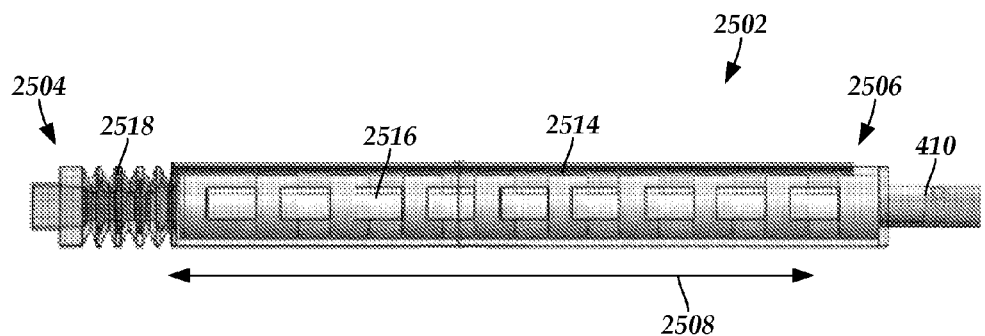
FIG. 25A is a schematic side view of a lead or lead extension inserted into a third embodiment of a connector of an electrical stimulation system, according to the invention.

FIGS. 4A, 13A, and 25A show three embodiments of connectors configured and arranged to receive leads or lead extensions. In at least some embodiments, conductive contacts disposed in the connectors are configured and arranged to couple electrically to terminals disposed on the leads or lead extensions when the leads or lead extensions are inserted into the connectors. It will be understood that the connectors may be disposed in many different locations including, for example, on lead extensions, lead adapters, lead splitters, the connector portion of control modules, or the like. In preferred embodiments, the connectors are disposed on the distal ends of lead extensions. It will be understood that, depending on the location of the connector, one or more components of the connector may be omitted from the connector. For example, connectors disposed on control modules typically do not include strain relief arrangements.

Each of the embodiments of the connectors shown in FIGS. 4A, 13A, and 25A include components (e.g., retaining elements, windows, strain relief arrangements, end stops, or the like) described in relation to one particular embodiment of the connector. It will be understood that, although a component may only be described in relation to only one of the embodiments of the connectors shown in FIGS. 4A, 13A, and 25A, the component may apply equally to one or more of the other embodiments of the connectors shown in FIGS. 4A, 13A, and 25A.

FIG. 4A is a schematic side view of one embodiment of a connector 402 of an electrical stimulation system, the connector having a first end 404, a second end 406, and a length 408, shown in FIG. 4A as a two-headed arrow. A proximal end of a lead or lead extension 410 is insertable into the connector 402. In at least some embodiments, the lead or lead extension 410 is insertable into the second end 406 of the connector 402. In at least some embodiments, the connector 402 includes a retaining element 412 configured and arranged to retain the lead or lead extension 410 within the connector 402. The connector 402 may also include a connector housing 414 defining an array of optional viewing apertures, such as viewing aperture 416. A transparent or translucent material (e.g., polycarbonate, or the like) may be disposed over at least a portion of the connector housing 414 such that the portions of the transparent or translucent material disposed over the apertures 416 forms windows through which a practitioner can view one or more portions of the lead or lead extension 410 when the lead or lead extension 410 is disposed in the connector 402.

In at least some embodiments, the connector 402 includes one or more strain relief arrangements 418 disposed along at least one portion of the connector 402. The strain relief arrangement 418 is configured and arranged to expand and contract along the length 408 to absorb strain potentially placed on the connector 402 by patient movement. In at least some embodiments, at least one of the one or more strain relief arrangements 418 is disposed at the first end 404 of the connector 402. In at least some embodiments, the strain relief arrangement 418 is formed as a portion of the connector housing 414.

It will be understood that one or more of the components (e.g., the retaining element 412, the apertures 416, the one or more strain relief arrangements 418, the one or more end stops 424, or the like) of the connector 402 discussed above may be positioned in alternate positions from the positions shown in FIG. 4A. For example, in FIG. 4A the retaining element 412 is shown disposed at the second end 406 of the connector 402. It will be understood, however, that the retaining element 412 may be disposed anywhere along the length 408 of the connector 402. It will also be understood that the connector 402 may include more than one retaining element 412. It will further be understood that the same lack of constraints for the placement and numbers of components (e.g., the retaining element 412, the apertures 416, the one or more strain relief arrangements 418, or the like) along the length 408 of the connector 402 applies equally to the connectors of FIGS. 13A and 25A, as well.

When the connector 402 is disposed on a control module (e.g., connector 144 of FIGS. 1-3A), conductive wires (or optionally other types of conductors) extending from connector contacts disposed within the connector 402 may couple the connector contacts electrically to an electronic subassembly (3610 of FIG. 6) within the control module. When the connector 402 is part of a lead extension and is coupled to the distal end of the lead extension (e.g., the connector is attached at the distal end 326 of lead extension 324 of FIG. 3B). In which case, the lead extension may include a plurality of conductive wires that electrically couple the connector contacts disposed within the connector 402 to a proximal end of the lead extension that is opposite to the distal end. In at least some embodiments, the conductive wires disposed in the lead extension can be electrically coupled to a plurality of terminals disposed on the proximal end of the lead extension. In at least some embodiments, the proximal end of the lead extension is configured and arranged for insertion into a connector disposed in another lead extension. The proximal end of the lead extension may be configured and arranged for insertion into another connector disposed on a control module (e.g., connector 144 of FIGS. 1-3A).

Figure 4B:
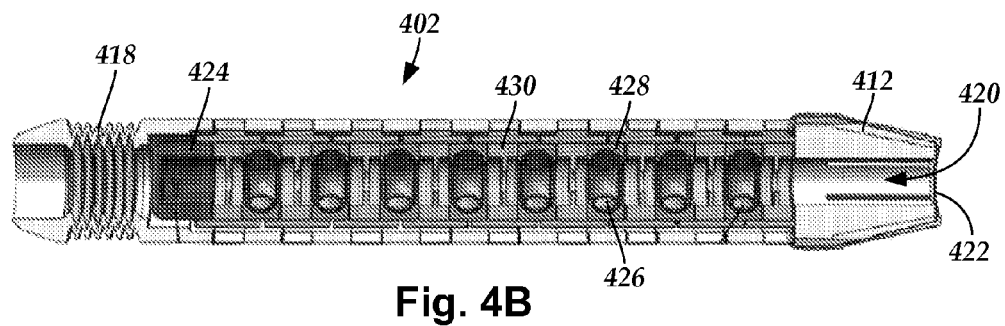
FIG. 4B is a schematic longitudinal cross-sectional view of one embodiment of the connector of FIG. 4A, according to the invention.

FIG. 4B is a longitudinal cross-sectional view of one embodiment of the connector 402. The connector 402 includes a port 420 extending from a port access 422 to an end stop 424. The port 420 is configured and arranged to receive the proximal end of the lead or lead extension 410. An array of connector contacts, such as connector contact 426, are disposed in contact housings, such as contact housing 428, such that the connector contacts 426 are exposed to the port 420. One or more non-conductive spacers, such as spacer 430, are disposed between adjacent connector contacts 426 and contact housings 428. The spacers 430 and connector contacts 426/contact housings 428 can be configured into any suitable arrangement for coupling with an inserted lead or lead extension 410 depending on the construction of 410.

The connector contacts 426 can be formed from any suitable conductive material suitable for implantation (e.g., one or more metals, alloys, conductive polymers, conductive carbon, or the like or combinations thereof). The contact housing 428 can be formed from any suitable conductive material suitable for implantation and for at least partially retaining inserted connector contacts 426. The spacers 430 can be formed from any suitable non-conductive material suitable for implantation (e.g., one or more non-conductive polymers, silicone, or the like or combinations thereof).

Figure 4C:
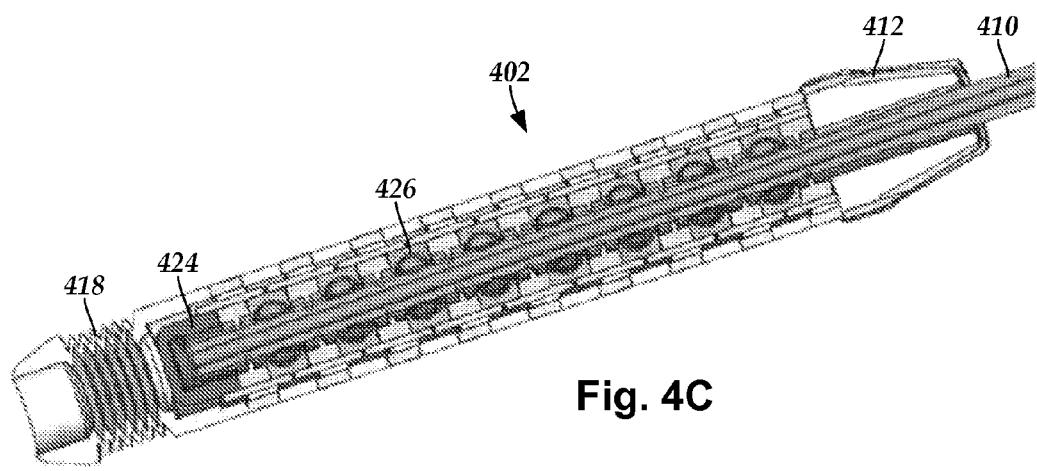
FIG. 4C is a schematic longitudinal cross-sectional view of one embodiment of a lead or lead extension inserted into the connector of FIG. 4A, according to the invention.

FIG. 4C is a schematic longitudinal cross-sectional view of one embodiment of the lead or lead extension 410 inserted into the connector 402. In FIG. 4C, the lead 410 is fully inserted into the connector 402 such that a proximal end of the lead or lead extension 410 is contacting the end stop 424. In at least some embodiments, the spacing between adjacent connector contacts is equal to a spacing between adjacent terminals of the received lead or lead extension 410. In at least some embodiments, the connector contacts 426 are spaced apart from one another such that when the lead or lead extension 410 is inserted into the port 420 until a proximal end of the lead or lead extension 410 contacts the end stop 424, the connector contacts 426 align with terminals disposed on the received lead or lead extension 410.

Figure 5A:
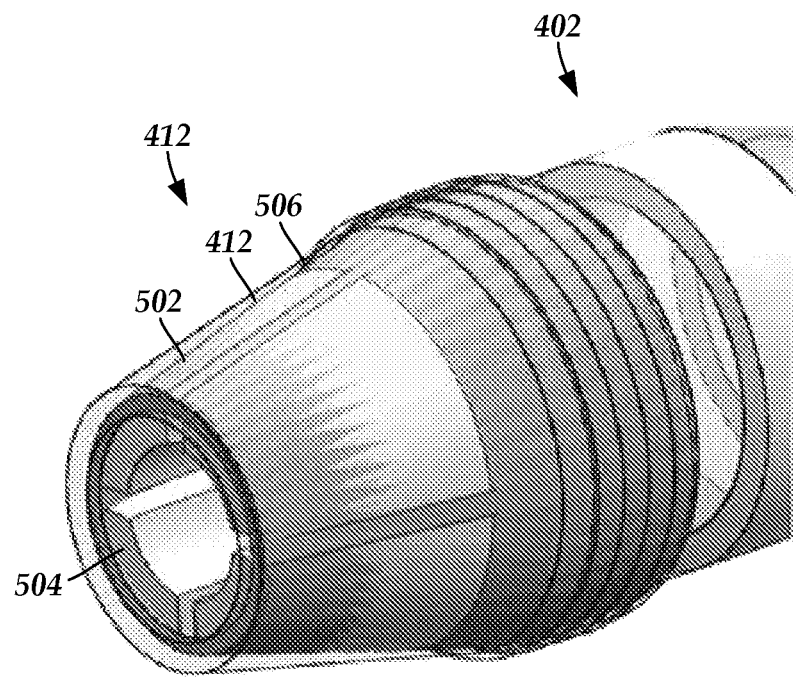
FIG. 5A is a schematic perspective view of one embodiment of a retaining element suitable for use with the connector of FIG. 4A, according to the invention.
Figure 5B:
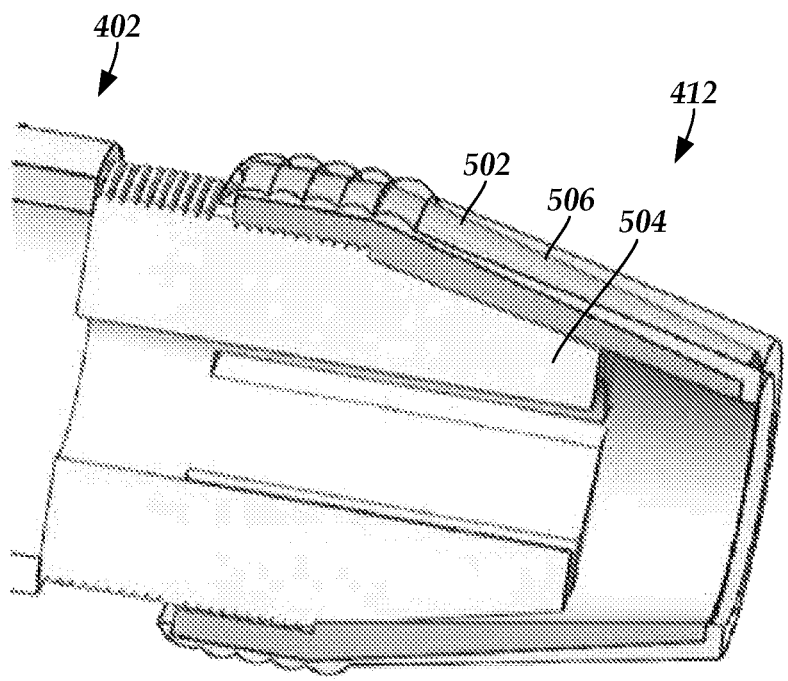
FIG. 5B is a schematic longitudinal cross-sectional view of one embodiment of the retaining element of FIG. 5A, according to the invention.

The connector 402 can be formed with any type of retaining element 412 suitable for retaining the lead or lead extension 410 within the connector 402. FIG. 5A is a schematic perspective close-up view of one embodiment of the retaining element 412. FIG. 5B is a schematic longitudinal cross-sectional view of the embodiment of the retaining element 412 shown in FIG. 5A. The retaining element 412 operates as a pin vice. In FIGS. 5A-5B, the retaining element 412 includes a collar 502 that couples with a corresponding region of a plurality of jaws 504 extending from the distal end 408 of the connector 402. In at least some embodiments, the collar 502 is conical-shaped.

In at least some embodiments, the collar 502 is threaded and the corresponding region of the jaws 504 includes a corresponding threaded region (see e.g., FIG. 5B). In which case, rotation of the threaded collar 502 in a first direction along the corresponding threaded portion of the jaws 504 causes the jaws 504 to open, thereby allowing insertion or removal of the lead or lead extension 410 from the connector 410. Meanwhile, rotation of the threaded collar 502 in a second direction along the corresponding threaded portion of the jaws 504 causes the jaws 504 to close due to the slope of the collar 502, thereby tightening against (and retaining) the lead or lead extension 410 when the lead or lead extension 410 is inserted into the connector 402.

The collar 502 and the jaws 504 are formed from hard durable materials, such as metal or plastic. In at least some embodiments, a membrane 506 is disposed over the collar 502. In at least some embodiments, the membrane 506 forms a gripping surface (e.g., one or more ridges, protrusions, grooves, or the like) for facilitating rotation of the collar 502 to open or close the jaws 504. In at least some embodiments, the membrane 506 is formed from silicone.

The connector can be formed with any type of conductor contact. As discussed above, it may be advantageous to form the connector with connector contacts that increase the likelihood of maintaining contact with terminals of an inserted lead or lead extension, despite small misalignments. FIG. 7A is a schematic side view and a longitudinal cross-sectional view of one embodiment of the connector contact 426. As shown in FIG. 7A, the connector contact 426 is toroidal-shaped and has an elliptical cross section. An elliptical cross-section may have a wider contact surface than a similarly-sized connector contact with a round cross-section. Thus, forming the connector contact 426 with an elliptical cross-section may increase the likelihood of maintaining contact with terminals of an inserted lead or lead extension, despite small misalignments.

In at least some embodiments, the connector contact 426 is formed as a wound spring formed into a torus instead of having a solid external surface, as shown in FIG. 7A. In at least some embodiments, forming the connector contact 426 with an elliptical cross-section may increase compressibility of the connector contact 426 along the plane of the connector contact 426.

FIG. 7B is a schematic longitudinal cross-sectional view of one embodiment of the lead or lead extension 410 inserted into a portion of the connector 402. The portion of the connector (402 in FIG. 4B) shown in FIG. 7B includes the connector contact 426 disposed in the contact housing 430. The spacer 430 is disposed adjacent to the connector contact 426 and contact housing 430.

As discussed above, it may be advantageous to enable a medical practitioner to identify when terminals of the lead or lead extension are aligned with connector contacts of the connector when the proximal end of the lead or lead extension is inserted into the connector. FIG. 8A is a schematic perspective view of one embodiment of a portion of the connector housing 414. The connector housing 414 includes the array of apertures 416. In at least some embodiments, the windows are spaced apart from one another such that the apertures 416 align with the spacers 430 disposed within the connector 402 and the portions of the connector housing 414 disposed between the apertures 416 align with connector contacts 426 disposed within the connector 402.

Figure 8B:
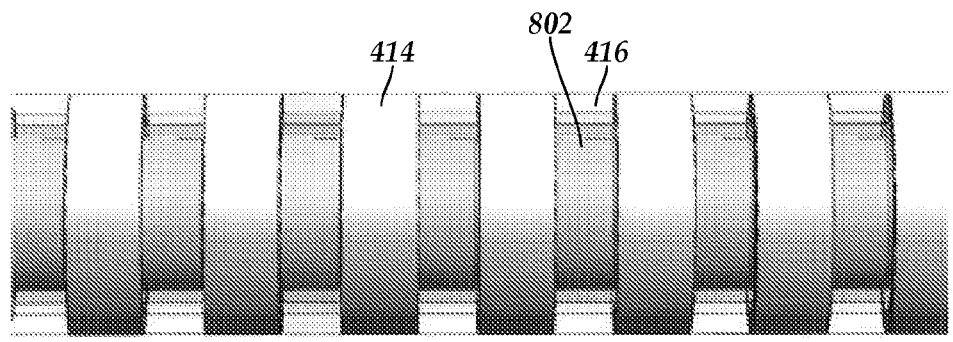
FIG. 8B is a schematic top view of one embodiment of a portion of the connector housing of FIG. 8A with window-covered apertures, according to the invention.
Figure 8C:
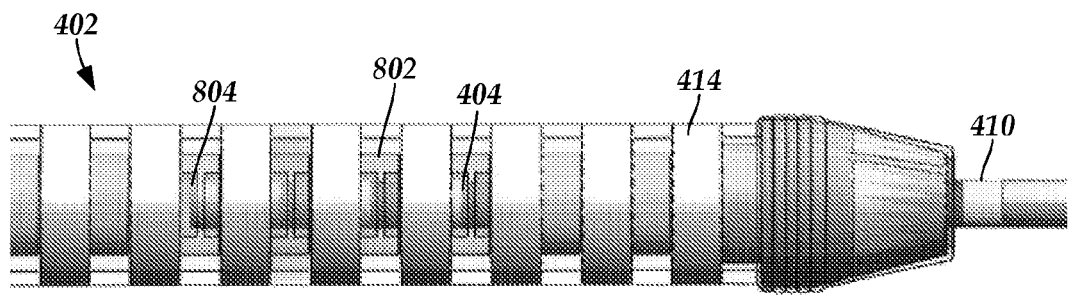
FIG. 8C is a schematic side view of one embodiment of a portion of a lead or lead extension inserted into the contact housing of FIG. 8A, wherein portions of the lead or lead extension are visible from an exterior of the contact housing through some of the windows, according to the invention.

FIG. 8B is a schematic top view of one embodiment of the transparent or translucent material (e.g., polycarbonate, or the like) disposed over a portion of the connector housing 414 such that the transparent or translucent material is disposed over the apertures 416 to form windows 802. FIG. 8C is a schematic side view of one embodiment of one embodiment of the lead or lead extension 410 inserted into the connector 402 such that a practitioner can view one or more portions of the lead or lead extension 410 through the windows 802.

In at least some embodiments, the apertures 416 and corresponding windows 802 provide visual feedback to a medical practitioner by enabling the medical practitioner to see inside portions of the connector 402. Being able to see inside portions of the connector 402 may be especially beneficial during insertion of the lead or lead extension 410 into the connector 402.

In at least some embodiments, the windows 802 enable a medical practitioner to gauge how far the lead or lead extension 410 is inserted into the connector 402 by enabling the medical practitioner to see the location of a proximal end 804 of the lead or lead extension 410 within the connector 402. In at least some embodiments, the windows 802 enable a medical practitioner to gauge the degree of alignment between terminals of the lead or lead extension 410 and the connector contacts 426 of the connector 402 by enabling the medical practitioner to see whether the terminals or the spacers between the terminals of the lead or lead extension 410 are visible through the windows 802. The windows 802 can be formed from any suitably transparent or translucent, flexible, biocompatible material including, for example, polyurethane, clear silicone, or other polymer.

Figure 9:
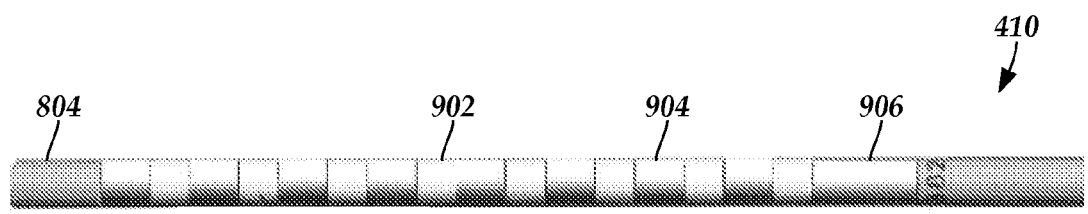
FIG. 9 is a schematic side view of one embodiment of a lead or lead extension suitable for insertion into the connector of FIG. 4A, according to the invention.

FIG. 9 is a schematic side view of one embodiment of the lead or lead extension 410. In at least some embodiments, the lead or lead extension 410 is formed so as to increase visibility of the lead or lead extension 410 within the connector 402. In FIG. 9, non-conductive spacers, such as spacer 902, are disposed between adjacent terminals 904. In at least some embodiments, the spacers 902 are formed from one or more visually distinct colors (or other surface ornamentation) that are visible beneath the windows 802. In at least some embodiments, the surface ornamentation of the spacers 902 may vary along the length of the array of terminals 904. In which case, different surface ornamentation (or other distinct features, such as shapes, patterns, colors, or the like) may be used as a code to enable a practitioner to determine not only whether or not one of the plurality of terminals 904 of the inserted lead or lead extension 410 is aligned with one of the connector contacts 426, but also to determine whether a particular terminal of the plurality of terminals 904 is aligned with one of the connector contacts 926, thereby allowing the practitioner to determine whether or not the inserted lead or lead extension 410 is fully inserted into the connector 402.

In at least some embodiments, the lead or lead extension 410 further includes a retention sleeve 906 disposed distally from the terminal array 904. The retention sleeve 906 is typically formed from a metallic material and is not connected to any conductor wires. A screw or protrusion is typically moved into place to abut against the retention sleeve to hold the lead or lead extension 410 in the connector 402. In at least some embodiments, a fastener (see e.g., fastener 1402 of FIG. 14) inserted into the retaining element 412 contacts, and tightens against, the retention sleeve 906, thereby retaining the lead or lead extension 410 in the connector 402.

In at least some embodiments, when the lead or lead extension 410 is inserted into the port 420 of the connector 402, the end stop 424 is disposed at the proximal-most position of the port 420 to provide a proximal-most point of insertion for the lead or lead extension 410. In at least some embodiments, the end stop 424 includes a feedback mechanism to notify the medical practitioner when the proximal end 804 of the lead or lead extension 410 is contacting the end stop. In at least some embodiments, the feedback mechanism provides tactile feedback to the medical practitioner when the proximal end 804 of the lead or lead extension 410 contacts the end stop 424. In at least some embodiments, the feedback mechanism provides audible feedback to the medical practitioner when the proximal end 804 of the lead or lead extension 410 contacts the end stop 424.

Figure 10A:
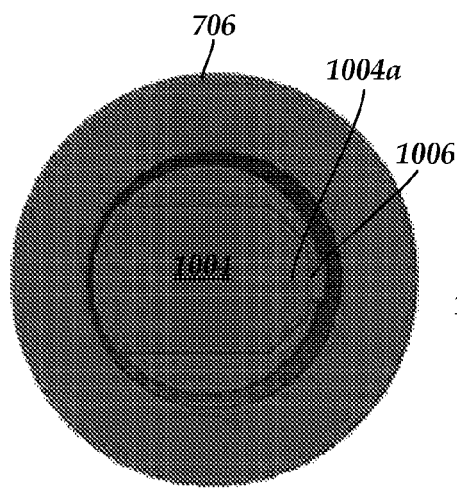
FIG. 10A is a schematic top view of one embodiment of an end stop suitable for use with the connector of FIG. 4A, according to the invention.
Figure 10B:
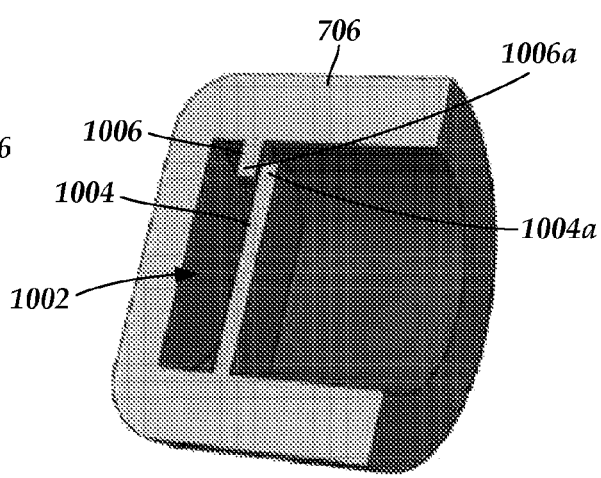
FIG. 10B is a schematic perspective, longitudinal cross-sectional view of one embodiment of a feedback mechanism disposed in the end stop of FIG. 10A, according to the invention.

FIG. 10A is a schematic top view of one embodiment of the end stop 424. FIG. 10B is a schematic perspective, longitudinal cross-sectional view of this end stop 424. The end stop 424 includes a feedback mechanism 1002. The feedback mechanism 1002 includes a first tab 1004 and a second tab 1006. The first tab 1004 includes a distal end 1004a and extends in a direction that is substantially transverse to the length 408 of the connector 402. In at least some embodiments, the second tab 1006 includes a distal end 1006a and extends in a direction that is also substantially transverse to the length 408 of the connector 402.

The first tab 1004 and the second tab 1006 extend from opposite sides of the end stop 706 such that distal ends 1004a, 1006a of the first tab 1004 and the second tab 1006, respectively, overlap one another. In preferred embodiments, the first tab 1004 and the second tab 1006 are different sizes and the distal ends 1004a, 1006a of the two tabs 1004, 1006, respectively, overlap one another such that the larger of the two tabs 1004, 1006 is proximal to the smaller of the two tabs 1004, 1006 with respect to the length 408 of the connector 402. In FIGS. 10A-10B, the first tab 1004 is shown as being the larger of the two tabs 1004, 1006.

In at least some embodiments, during insertion of the lead or lead extension 410 inserted into the connector 402, when the proximal end 1804 of the lead or lead extension 410 contacts the first tab 1004 with enough force, the distal end 1004a of the first tab 1004 bends distally with respect to the length 408 of the connector 402 past the distal end 1006a of the second tab 1006.

In at least some embodiments, when the distal end 1004a of the first tab 1004 bends distally past the distal end 1006a of the second tab 1006 with respect to the length 408 of the connector 402, audible feedback is provided to the medical practitioner inserting the lead or lead extension 410 into the connector 402. In at least some embodiments, an audible sound, such as a clicking sound, occurs when the distal end 1004a contacts and passes behind the distal end 1006a.

In at least some embodiments, when the distal end 1004a of the first tab 1004 bends distally past the distal end 1006a of the second tab 1006 with respect to the length 408 of the connector 402, tactile feedback is provided to the medical practitioner inserting the lead or lead extension 410 into the connector 402. In at least some embodiments, when the lead or lead extension 410 is removed from the connector 402, the distal end 1004a of the first tab 1304 moves back proximally with respect to the length 408 of the connector 402 such that the distal end 1004a of the first tab 1004 is positioned proximal to the distal end 1006a of the second tab 1006 with respect to the length 408 of the connector 402.

Figure 11A:
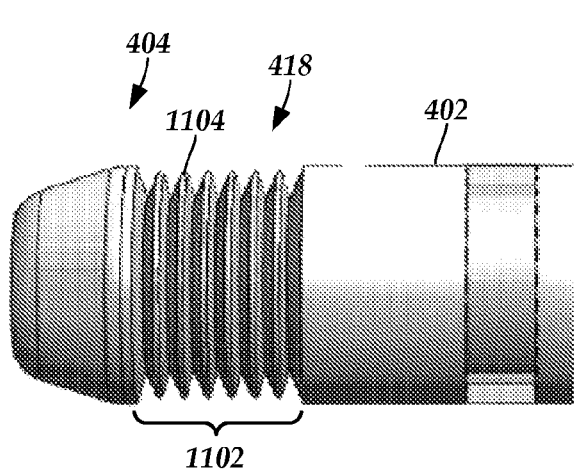
FIG. 11A is a schematic side view of one embodiment of an expandable strain relief arrangement suitable for use with the connector of FIG. 4A, according to the invention.

Turning to FIG. 11A, as discussed above patient movement may eventually cause the lead or lead extension inserted into the connector to loosen, or even disconnect from the connector 402, thereby reducing, or even completely discontinuing, the therapeutic effects of the electrical stimulation system. For example, loosening of the lead or lead extension within the connector may cause terminals of the lead or lead extension to become partially, or even fully, misaligned with connector contacts disposed in the connector. It may, therefore, be advantageous to form the connector such that when the lead or lead extension is inserted into the connector, the inserted lead or lead extension is more likely to remain inserted into the connector despite bending, twisting, and stretching caused by patient movement over time.

Figure 11B:
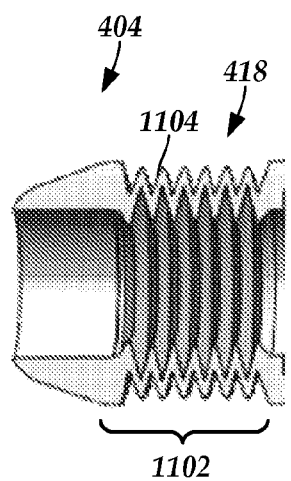
FIG. 11B is a schematic longitudinal cross-sectional view of one embodiment of the expandable strain relief arrangement of FIG. 11A, according to the invention.

FIG. 11A is a schematic side view of one embodiment of the expandable strain relief arrangement 418 disposed at the first end 404 of the connector housing 414. FIG. 11B is a schematic longitudinal cross-sectional view of one embodiment of the expandable strain relief arrangement 418. In at least some embodiments, the strain relief arrangement 418 includes an accordion-like section 1102 that includes array of interconnected pleats, such as pleat 1104. The pleats 1104 in the accordion-like section 1102 can expand and contract with patient movement, thereby at least partially dampening tension created by patient movement from being transferred to the connector 402 from the inserted lead or lead extension 410.

Figure 11C:
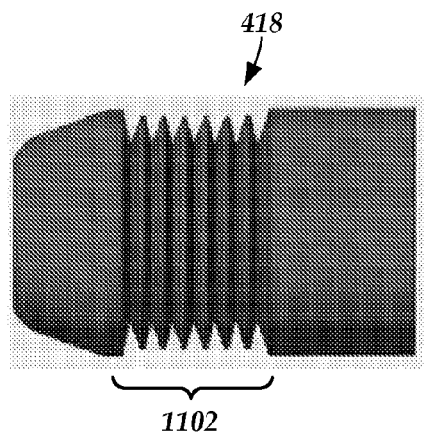
FIG. 11C is a schematic side view of one embodiment of the expandable strain relief arrangement of FIG. 11A in a relaxed position, according to the invention.
Figure 11D:
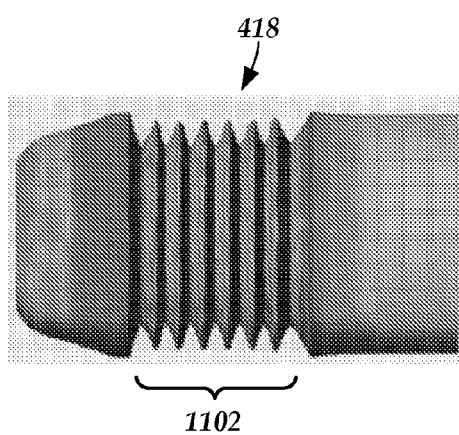
FIG. 11D is a schematic side view of one embodiment of the expandable strain relief arrangement of FIG. 11A in an expanded position, according to the invention.
Figure 11E:
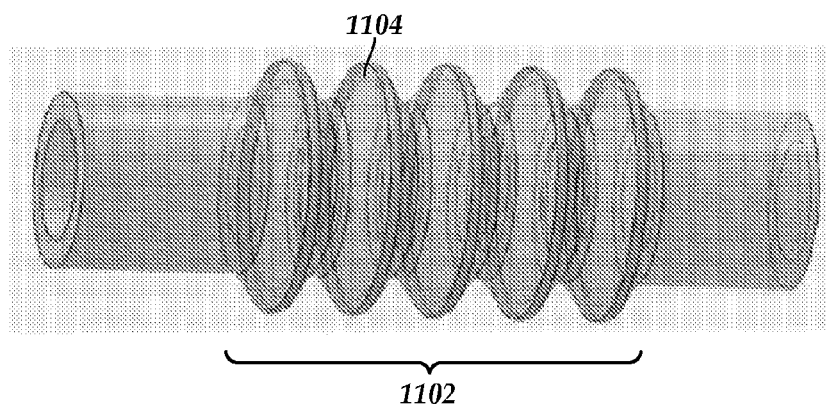
FIG. 11E is a schematic perspective view of another embodiment of an expandable strain relief arrangement suitable for use with the connector of FIG. 4A, according to the invention.

FIG. 11C is a schematic side view of one embodiment of the strain relief arrangement 418, where the pleats 1104 are in a relaxed position. FIG. 11D is a schematic side view of one embodiment of the strain relief arrangement 418, where the pleats 1104 are expanded in response to two or more opposing forces. In at least some embodiments, as shown in FIGS. 11A-11C, the pleats 1104 of the accordion-like section have transverse diameters that are no greater than transverse diameters of the connector housing 414. In alternate embodiments, as shown in FIG. 11E, the strain relief arrangement 418 may be formed such that one or more of the pleats 1104 have transverse diameters that are larger than the transverse diameter of the connector housing 414.

Figure 12A:
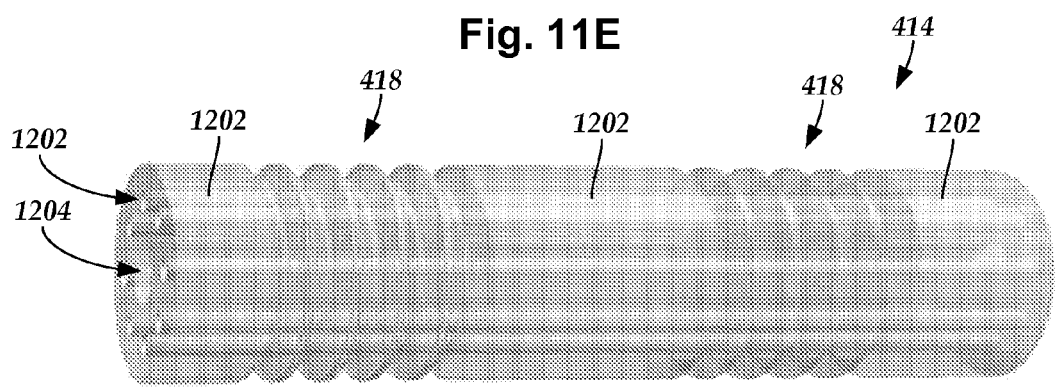
FIG. 12A is a schematic perspective view of one embodiment of a portion of a connector housing, the portion of the contact housing including an expandable strain relief arrangement and defining a plurality of lumens, according to the invention.

Turning to FIG. 12A, in at least some embodiments the connector contacts 426 are electrically coupled to conductive wires that extend to the first end 404 of the connector 402. In at least some embodiments, when the connector is part of a distal end of a lead extension, the conductive wires coupled to the connector contacts may extend to terminals on a proximal end of the lead extension (see e.g., FIG. 3B). In at least some embodiments, one or more lumens may be defined in the first end 404 of the connector 402. In at least some embodiments, the one or more lumens may be configured and arranged to receive the conductive wires (or other conductors) extending from the connector contacts 710 to the first end 404 of the connector 402. In at least some embodiments, the one or more lumens extend through at least one of the one or more strain relief arrangements 418.

FIG. 12A is a schematic perspective view of one embodiment of the first end 404 of the connector 402. Lumens 1202 may be defined the connector housing 414. The lumens 1202 extend within the strain relief arrangement 418. FIG. 12A shows two strain relief arrangements 418 disposed on the connector 402. Any number of strain relief arrangements 418 may be disposed on the connector 402. It will also be understood that the second end 406 of the connector 402 may define one or more additional lumens, such as lumen 1204, which may be a lumen configured and arranged to receive a stylet.

In at least some embodiments, the conductive wires extend along the lumens 1202 in relatively-straight configurations.

In at least some embodiments, the conductive wires may include one or more sections that include some slack, or that are coiled, or folded onto themselves to accommodate potential changes in length of the strain relief arrangement 418 when the strain relief arrangement 418 is stretched.

Figure 12B:
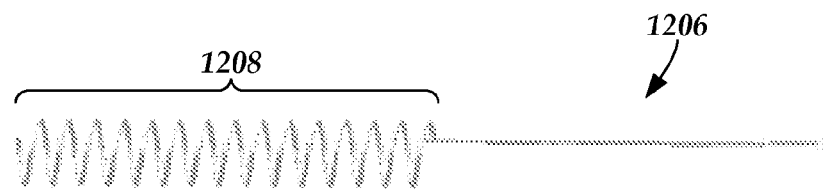
FIG. 12B is a schematic side view of one embodiment of a conductive wire suitable for insertion into the lumens of FIG. 12A, the conductive wire including a coiled portion, according to the invention.

FIG. 12B is a schematic side view of one embodiment of a portion of an exemplary conductive wire 1206 suitable for insertion into one of the lumens 1202. The conductive wire 1206 includes a non-linear section 1208 (e.g., coiled, folded, or the like) configured and arranged to align with the strain relief arrangement 418 when the conductive wire 1206 is disposed in one of the lumens 1202.

Figure 12C:
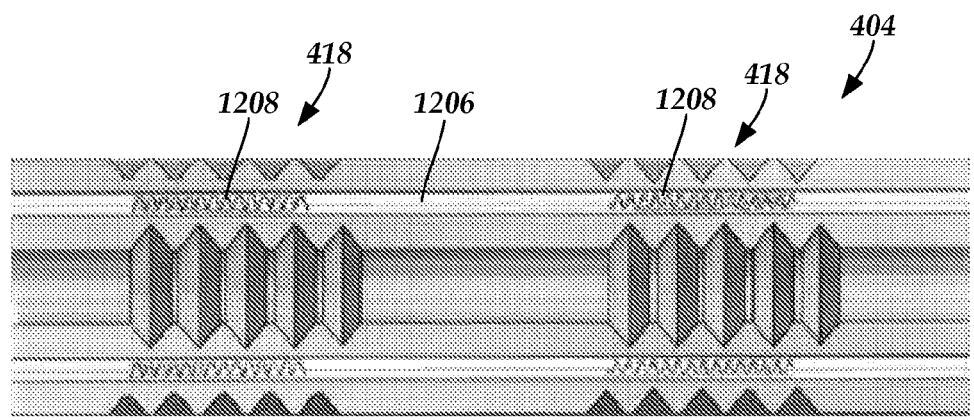
FIG. 12C is a schematic longitudinal cross-sectional view of one embodiment of the portion of a connector housing of FIG. 12A with conductive wires of FIG. 12B inserted into the lumens defined in the contact housing, according to the invention.

FIG. 12C is a schematic longitudinal cross-sectional view of one embodiment of conductive wires 1206 disposed in lumens 1202 such that non-linear sections 1208 of each of the conductive wires 1206 aligns with the respective strain relief arrangement 418. It will be understood that, in at least some embodiments, multiple conductive wires extend along each of one or more of the lumens 1206.

FIG. 13A is a schematic side view of another embodiment of a connector 1302 of an electrical stimulation system, the connector having a first end 1304, a second end 1306, and a length 1308, shown in FIG. 13A as a two-headed arrow. The lead or lead extension 410 is inserted into the second end 1306 of the connector 1302. In at least some embodiments, the connector 1302 includes a retaining element 1312 configured and arranged to retain the lead or lead extension 1304 within the connector 1302. In at least some embodiments, the connector 1302 includes a connector housing 1314 defining an array of apertures, such as aperture 1316. In at least some embodiments, a transparent or translucent material (e.g., polycarbonate, or the like) is disposed over at least a portion of the connector housing 1314 such that the portions of the transparent or translucent material disposed over the apertures 1316 forms windows through which a practitioner can view one or more portions of the lead or lead extension 410 when the lead or lead extension 410 is disposed in the connector 1302. In at least some embodiments, the connector housing 1314 includes a strain relief arrangement 1318.

Figure 13B:
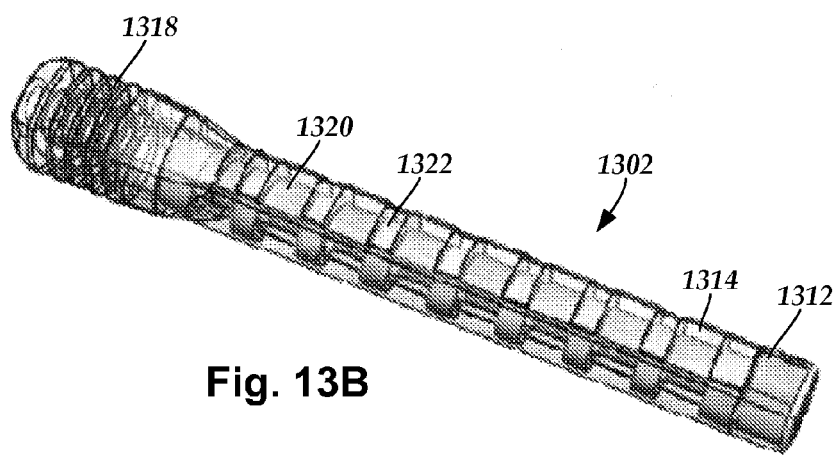
FIG. 13B is a schematic side view of one embodiment of the connector of FIG. 13A with a transparent connector housing for clarity of illustration, according to the invention.

FIG. 13B is a schematic side view of one embodiment of the connector 1302. In FIG. 13B, the connector 1302 is shown with a connector housing 1314. The connector housing 1314 is shown as being transparent in FIG. 13B for clarity of illustration. An array of contact housings, such as contact housing 1320, is disposed in the connector 1302. One or more non-conductive spacers, such as spacer 1322, are disposed between adjacent contact housings 1322.

Figure 13C:
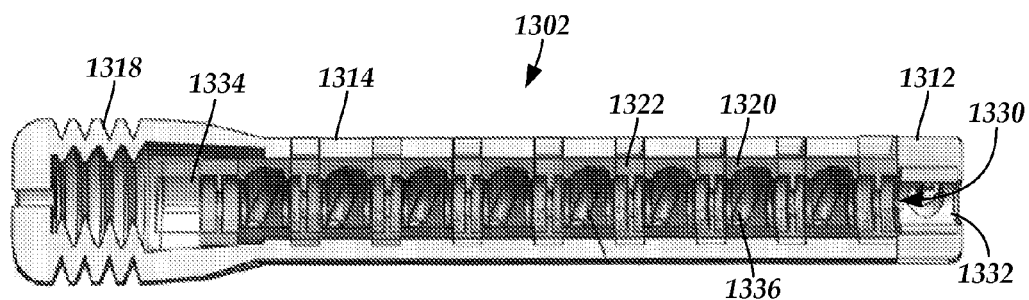
FIG. 13C is a schematic longitudinal cross-sectional view of one embodiment of the connector of FIG. 13A, according to the invention.

FIG. 13C is a schematic longitudinal cross-sectional view of one embodiment of the connector 1302. The connector 1302 includes a port 1330 extending from a port access 1332 to an end stop 1334. The port 1330 is configured and arranged to receive the lead or lead extension 410. One or more connector contacts, such as connector contact 1336, are disposed in each of the contact housings 1320 such that the connector contacts 1336 are exposed to the port 1330.

Figure 13D:
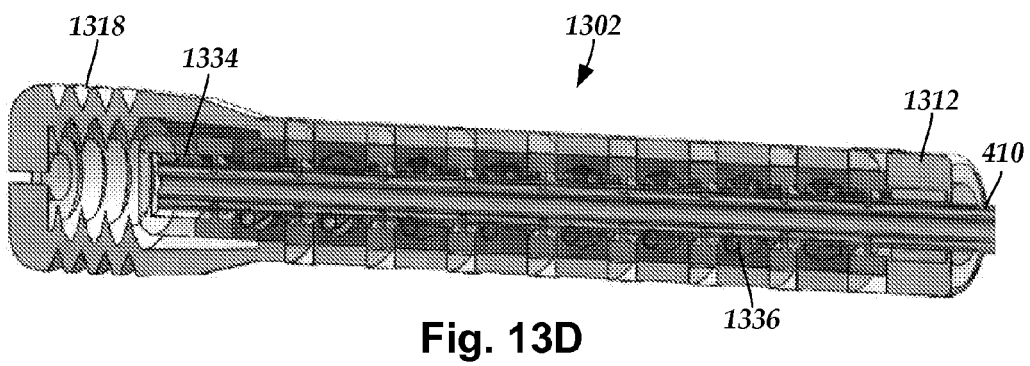
FIG. 13D is a schematic longitudinal cross-sectional view of one embodiment of a lead or lead extension inserted into the connector of FIG. 13A, according to the invention.

FIG. 13D is a schematic longitudinal cross-sectional view of one embodiment of a lead inserted into the connector 1302. In FIG. 13D, the lead or lead extension 410 is fully inserted into the connector 1302 such that a proximal end of the lead or lead extension 410 is contacting the end stop 1334. In at least some embodiments, the spacing between adjacent connector contacts 1336 is equal to the spacing between adjacent terminals of the received lead or lead extension 410. In at least some embodiments, the connector contacts 1336 are spaced apart from one another such that, when the lead or lead extension 410 is inserted into the port 1330 until a proximal end of the lead or lead extension 410 contacts the end stop 1334, the connector contacts 1336 align with, and contact, the terminals of the received lead or lead extension 410.

Figure 14:
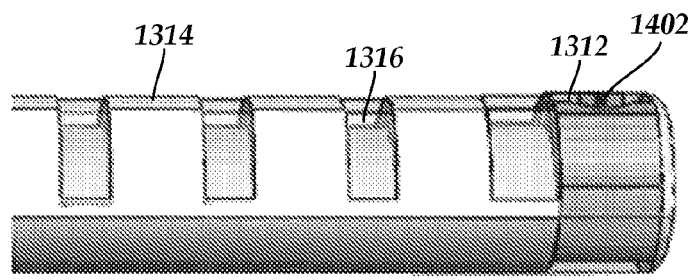
FIG. 14 is a schematic partial side view of one embodiment of a retaining element disposed on a proximal end of the connector of FIG. 13A, according to the invention.

FIG. 14 is a schematic partial side view of one embodiment of the retaining element 1312 disposed at a second end 1306 of the connector 1302. A fastener 1402 (e.g., a screw, pin, or the like), inserted into the retaining element 1312, is used for holding the proximal end of the lead or lead extension 410 in place while inserted into the connector 1302. It will be understood that retaining element 1312, as well as the previously-discussed retaining elements, can also be used with any of the other connector embodiments.

Figure 15:
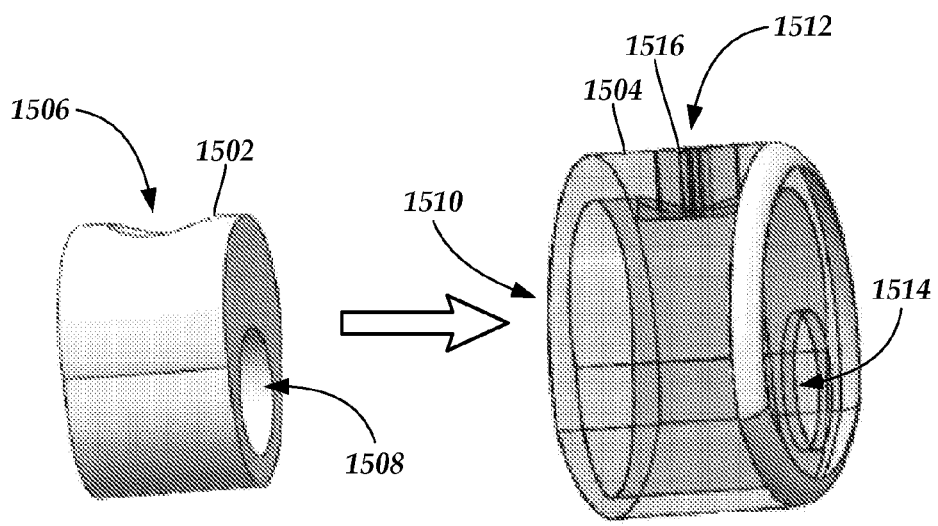
FIG. 15 is a schematic perspective exploded view of one embodiment of a fastener block and a corresponding septum that collectively form the retaining element of FIG. 13A, according to the invention.

FIG. 15 is a schematic perspective exploded view of one embodiment of the fastener block 1502 and an outer membrane 1504 configured and arranged to receive the fastener block 1502. The fastener block 1502 defines a fastener receiver 1506 for receiving the fastener 1402 and also defines a port aperture 1508 which forms the access 1332 for the port 1330. The outer membrane 1504 defines a cavity 1510 configured and arranged to receive the contact block 1502. The cavity 1510 defines a fastener aperture 1512 and a port aperture 1514. Thus, when the fastener block 1502 is inserted into the outer membrane 1504, the fastener 1402 can extend through the fastener aperture 1512 of the outer membrane 1504 and into the fastener receiver 1506 of the fastener block 1502. Additionally, when the fastener block 1502 is inserted into the outer membrane 1504, the lead or lead extension 410 can extend into the port aperture 1508 of the fastener block 1502 and the port aperture 1514 of the outer membrane 1504.

The fastener block 1502 can be formed from any hard material suitable to receive the fastener 1402 including, for example, metal, hard plastic, or the like. The outer membrane 1504 can be formed from any soft, pliable material suitable for protecting the fastener block 1502 including, for example, silicone. In at least some embodiments, the outer membrane 1504 has a transverse profile that is similar to a transverse profile of the connector housing 1314. In at least some embodiments, the outer membrane 1504 includes a septum 1516 disposed over the fastener aperture 1512 to provide a seal over the fastener 1402 when the fastener 1402 is inserted through the fastener aperture 1512 of the outer membrane 1504 and into the fastener receiver 1506 of the fastener block 1502. The outer membrane 1504 and the septum 1516 protect the fastener block 1502 and the corresponding inserted fastener 1402 from potentially deleterious effects caused by body fluids, such as corrosion, short-circuiting, or the like.

Figures 16A, 16B:
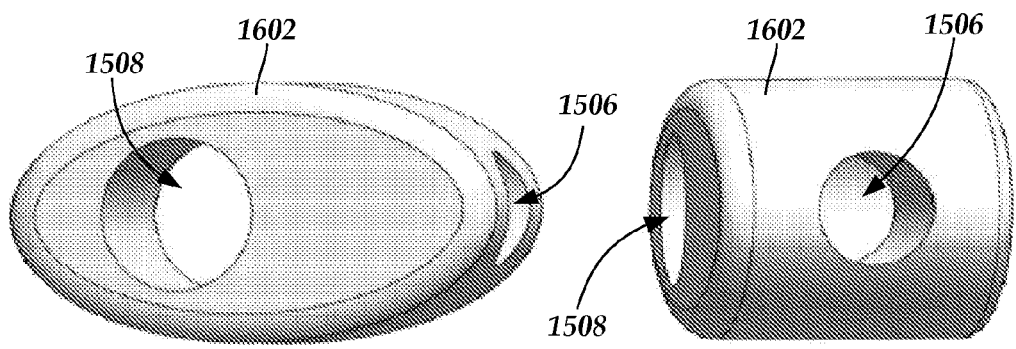
FIG. 16A is a schematic front perspective view of one embodiment of the fastener block of FIG. 15, according to the invention.
FIG. 16B is a schematic side perspective view of one embodiment of the fastener block of FIG. 15, according to the invention.

FIG. 16A is a schematic front perspective view of another embodiment of a fastener block 1602 suitable for use with the retaining element 1312. FIG. 16B is a schematic side perspective view of the fastener block 1602. The fastener block 1602 is similar to the fastener block 1502 with a different transverse shape than the fastener block 1502. The fastener block 1602 defines the fastener receiver 1506 for receiving the fastener 1402 and also defines the port aperture 1508.

As discussed above, it may be advantageous to form the connector with connector contacts that increase the likelihood of maintaining contact with terminals of the inserted lead or lead extension, despite small misalignments. FIG. 17A is a schematic side view of one embodiment of the contact housing 1320. FIG. 17B is a schematic perspective view of one embodiment of the contact housing 1320. In at least some embodiments, the contact housing 1320 does not extend completely around the port 1330. In at least some embodiments, the contact housing 1320 is C-shaped. In at least some embodiments, the contact housing 1320 defines an inset region 1702 suitable for receiving the connector contact 1336. In at least some embodiments, the inset region 1702 receives the connector contact 1336 such that the connector contact 1336 extends diagonally within the contact housing 1320.

FIG. 18A is a schematic perspective view of one embodiment of the connector contact 1336 disposed in the contact housing 1320. In at least some embodiments, the connector contact 1336 also does not extend completely around a circumference of the port 1330. In at least some embodiments, the contact housing 1320 is C-shaped.

Forming the contact housing 1320 such that the connector contact 1336 extends diagonally within the contact housing 1320 facilitates physical contact with terminals of the lead or lead extension 410 when the lead or lead extension 410 is inserted in the connector 1302, despite small misalignments between the terminals and the connector contacts 1336. Additionally, forming the contact housing 1320 and the connector contact 1336 disposed therein such that the contact housing 1320 and the connector contact 1336 do not extend completely around the port 1330 may enable the connector housing 1314 to be formed with a reduced profile while still providing suitable electrical contact to be made between the terminals and the connector contacts 1336.

FIG. 18B is a schematic longitudinal cross-sectional view of one embodiment of the lead or lead extension 410 inserted into a portion of the connector 1302. The portion of the connector 1302 shown in FIG. 13B includes the connector contact 1336 disposed in the contact housing 1320. The spacers 1322*a* and 1322*b* flank the connector contact 1336 and contact housing 1320.

In at least some embodiments, the connector 1302 has a transverse shape that is not round. In at least some embodiments, the connector housing 1314 has a transverse shape that is not round. In at least some embodiments, the connector housing 1314 has a circumference that includes at least two different opposing, connecting arced portions. In at least some embodiments, the circumference of the connector housing 1314 having the at least two different opposing, connecting arced portions is less than the circumference would be if either of the at least two different opposing, connecting arced portions were to be extended to form a complete circle. Thus, the circumference of the connector 1302 may be reduced by forming the connector housing from at least two different opposing, connecting arced portions.

In at least some embodiments, the transverse shape of the spacers 1322 is similar to the transverse shape of the connector housing 1314. In at least some embodiments, the transverse shape of the contact housings 1320 is similar to at least a portion of the connector housing 1314. In at least some embodiments, the transverse shape of the spacers 1322 is similar to at least a portion of the transverse shape of the contact housings 1320.

Figure 19:
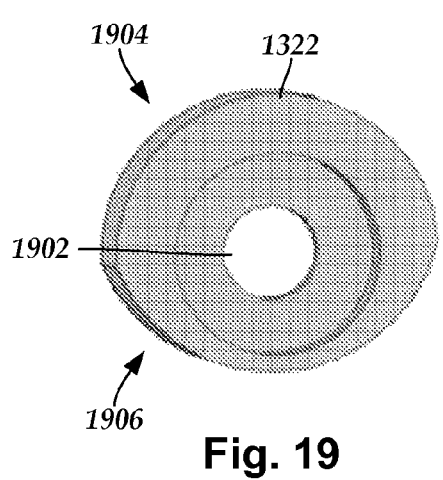
FIG. 19 is a schematic front view of one embodiment of a non-conductive spacer suitable for use with the connector of FIG. 13A, according to the invention.

FIG. 19 is a schematic front view of one embodiment of a spacer 1322. The spacer 1322 has an aperture 1902 and is aligned with other spacers 1322 and contacts 1320. In at least some embodiments, the spacer 1322 has a transverse shape that is not round. In at least some embodiments, the spacer 1322 includes a circumference with at least two different opposing, connecting arced portions 1904 and 1906.

Figure 20:
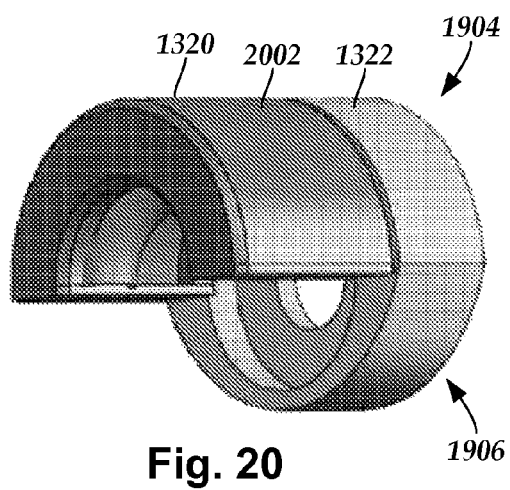
FIG. 20 is a schematic perspective view of one embodiment of the partially-cylindrical housing of FIG. 17A abutting the non-conductive spacer of FIG. 19, according to the invention.

FIG. 20 is a schematic perspective view of one embodiment of the contact housing 1320 abutting the spacer 1322. In at least some embodiments, the contact housing 1320 abuts the spacer 1322 such that the contact housing 1320 directly abuts only one of the arced portions 1904 and 1906 of the spacer 1322. In at least some embodiments, the contact housing 1320 is shaped such that an outer portion 2002 of the contact housing 1320 has a shape and size that is similar to the shape and size of one of the arced portions 1904 and 1906.

Figure 21A:
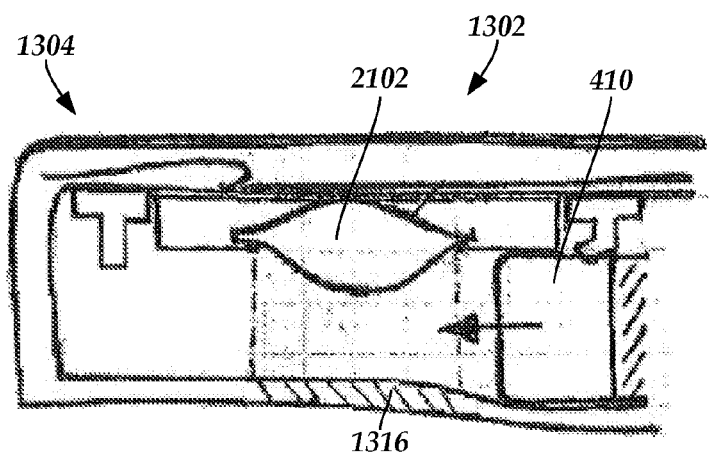
FIG. 21A is a schematic longitudinal cross-sectional view of another embodiment of a connector contact disposed in the connector of FIG. 13A, according to the invention.
Figure 21B:
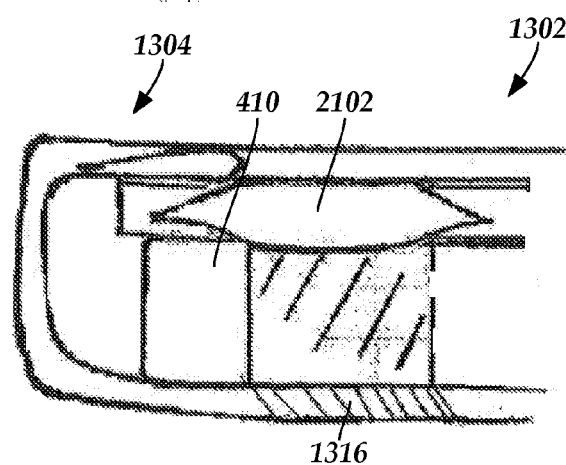
FIG. 21B is a schematic longitudinal cross-sectional view of one embodiment of a proximal end of a lead or lead extension inserted into the connector of FIG. 13A such that a terminal of the lead or lead extension is contacting the connector contact of FIG. 21A, according to the invention.

FIG. 21A is a schematic longitudinal cross-sectional view of another embodiment of a connector contact 2102 suitable for use with the connector 1302. The connector contact 2102 is disposed near the first end 1304 of the connector 1302. In FIG. 21A, the lead or lead extension 410 is shown partially inserted into the connector 1302 such that the lead or lead extension 410 does not contact the connector contact 2102. In FIG. 21B, the lead or lead extension 410 is shown inserted into the connector 1302 such that the lead or lead extension 410 is contacting the connector contact 2102.

The connector contact 2102 includes a flexible, conductive leaf spring disposed on one side of the connector 1302. As shown in FIG. 21B, the connector contact 2102 is configured and arranged to flatten when contacted by the lead or lead extension 410. In at least some embodiments, the connector contact 2102 is arc-shaped. In at least some embodiments, at least one of the window-covered apertures 1316 is disposed over the connector contact 2102. In at least some embodiments, a medical practitioner can identify whether or not one of the terminals of the lead or lead extension 410 is aligned with the connector contact 2102 by looking through the window-covered aperture 1316.

In at least some embodiments, one or more of the connector contacts disposed in the connector 1320 is similar to the connector contact 2102. In at least some embodiments, each connector contact in the connector 1320 is similar to the connector contact 2102. In at least some embodiments, the connector contact 2102 is disposed in the connector 1302 such that the connector contact 1320 is the proximal-most connector contact. In at least some embodiments, viewing one of the terminals of the lead or lead extension 410 through a proximal-most window-covered aperture 1316 indicates that the lead or lead extension 410 is fully inserted in the connector 1302.

Figure 22A:
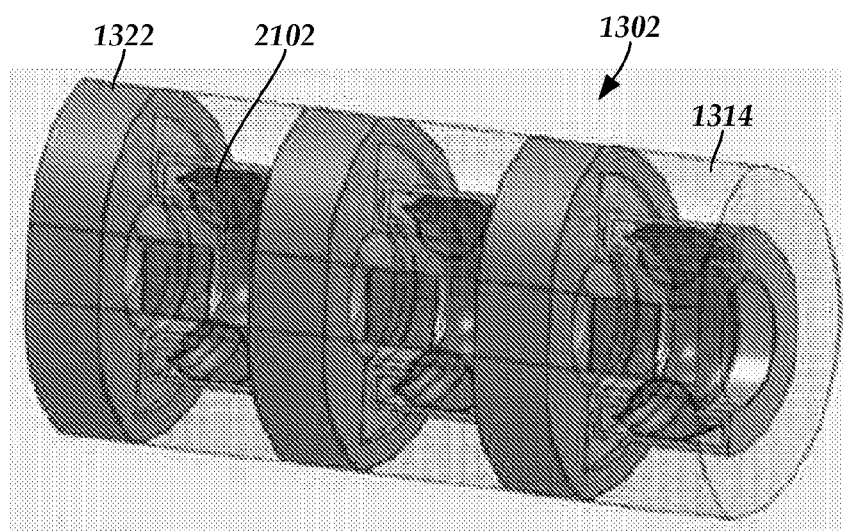
FIG. 22A is a schematic perspective, transparent, partial view of one embodiment of a portion of the connector of FIG. 13A, the connector including an array of the connector contacts of FIG. 21A disposed in a connector housing that includes an array of transparent regions, according to the invention.
Figure 22B:
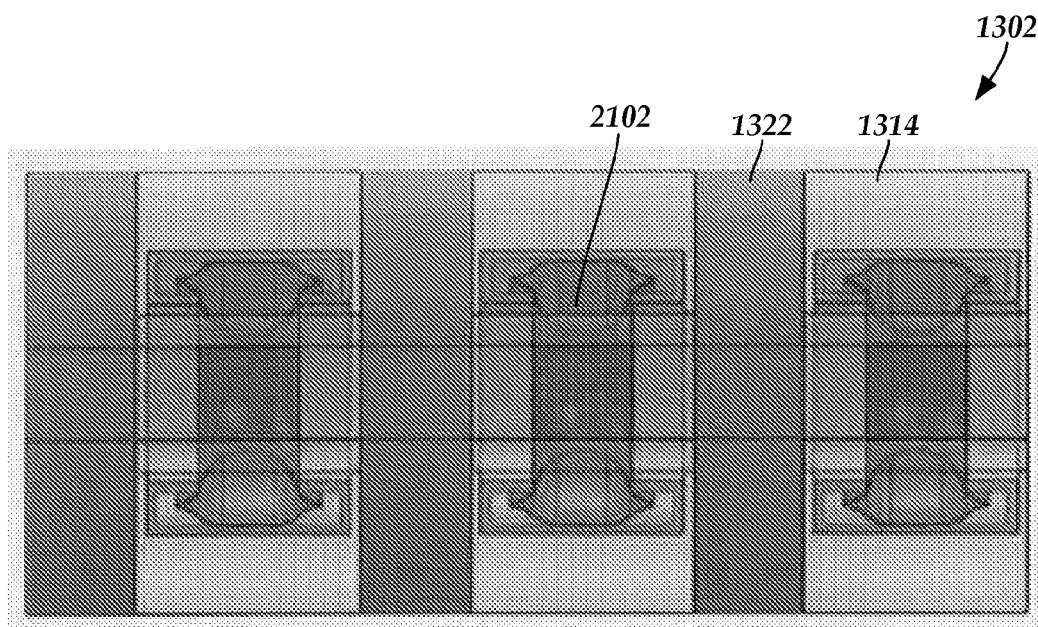
FIG. 22B is a schematic side view of one embodiment of a portion of the connector contacts of FIG. 21A disposed in the contact housing of FIG. 22A, according to the invention.

FIG. 22A is a schematic perspective, transparent, partial view of one embodiment of a portion of the connector 1302 with an array of connector contacts 2102 separated from one another by spacers 1322. FIG. 22B is a schematic side view of one embodiment of the connector 1302 with an array of connector contacts 2102 separated from one another by spacers 1322. The connector housing 1314 is transparent in FIGS. 22A-22B, for clarity of illustration.

FIG. 23 is a schematic side perspective view of one embodiment of the connector housing 1314. The connector housing 1314 defines the array of apertures 1316. In at least some embodiments, the array of apertures 1316 is configured and arranged such that the apertures 1316 are spaced apart from one another. In at least some embodiments, the apertures 1316 are spaced apart from one another such that the apertures 1316 align with the spacers 1322 disposed within the connector 1302 and the portions of the connector housing 1314 disposed between the apertures 1316 align with connector contacts 1336 disposed within the connector 1302.

In at least some embodiments, the connector housing 1314 has an outer shape that is not round. In at least some embodiments, the connector housing 1314 includes a circumference with at least two different opposing, connecting arced portions 2302 and 2304. In at least some embodiments, at least one of the one or more apertures 1316 is positioned over the end stop 1334. In at least some embodiments, a transparent or translucent material (e.g., polycarbonate, or the like) is disposed over at least a portion of the connector housing 1314 such that the portions of the transparent or translucent material disposed over the apertures 1316 forms windows through which a practitioner can view one or more portions of the lead or lead extension 410 when the lead or lead extension 410 is disposed in the connector 1302.

FIG. 24A is a schematic perspective view of one embodiment of the end stop 1334. In at least some embodiments, the end stop 1334 includes one or more transparent or translucent regions. In at least some embodiments, the entire end stop 1334 is transparent or translucent. FIG. 24B is a schematic perspective view of one embodiment of the first end 1304 of the connector 1302 with the lead or lead extension 410 inserted into the connector 1302. In at least some embodiments, at least a portion of the lead or lead extension 410 is visible through at least a portion of the end stop 1334. In at least some embodiments, at least a portion of the lead or lead extension is visible through the proximal-most windowed aperture 1316. It may be advantageous to see into the end stop 1334 to facilitate determination of whether or not the lead or lead extension 410 is fully inserted into the connector 1302.

FIG. 25A is a schematic side view of a third embodiment of a connector 2502 of an electrical stimulation system, the connector having a first end 2504, a second end 2506, and a length 2508, shown in FIG. 25A as a two-headed arrow. The lead or lead extension 410 is inserted into the second end 2506 of the connector 2502. The connector 2502 includes a retaining element (2512 in FIG. 25B) configured and arranged to retain the lead or lead extension 410 within the connector 2502. The connector 2502 also includes a connector housing 2514 defining an array of apertures, such as aperture 2516. In at least some embodiments, a transparent or translucent material (e.g., polycarbonate, clear silicone, or the like) is disposed over at least a portion of the connector housing 2514 such that the portions of the transparent or translucent material disposed over the apertures 2516 forms windows through which a practitioner can view one or more portions of the lead or lead extension 410 when the lead or lead extension 410 is disposed in the connector 2502.

In at least some embodiments, the connector housing 2514 includes a strain relief arrangement 2518 disposed at the first end 2504 of the connector housing 2514. The strain relief arrangement 2518 is configured and arranged to expand and contract along the length 2508 to absorb strain potentially placed on the connector 2502 by patient movement.

Figure 25B:
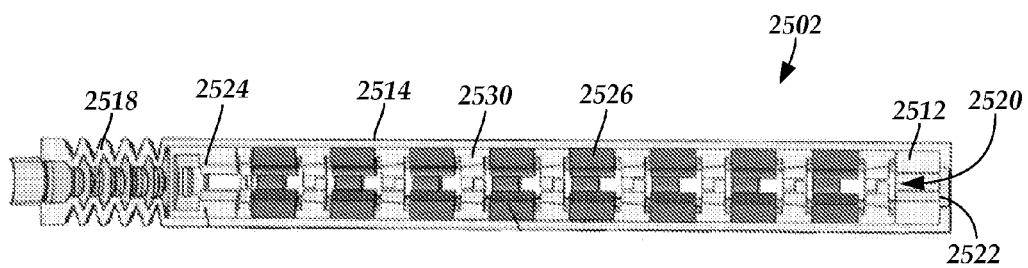
FIG. 25B is a schematic longitudinal cross-sectional view of one embodiment of the connector of FIG. 25A, according to the invention.

FIG. 25B is a schematic longitudinal cross-sectional view of one embodiment of the connector 2502. The connector 2502 includes a port 2520 extending from a port access 2522 to an end stop 2524. The port 2520 is configured and arranged to receive the lead or lead extension 410. Connector contacts, such as connector contact 2526, are disposed in the connector 2502 such that the connector contacts 2526 are exposed to the port 2520. One or more non-conductive spacers, such as spacer 2530, are disposed between adjacent connector contacts 2526.

Figure 25C:
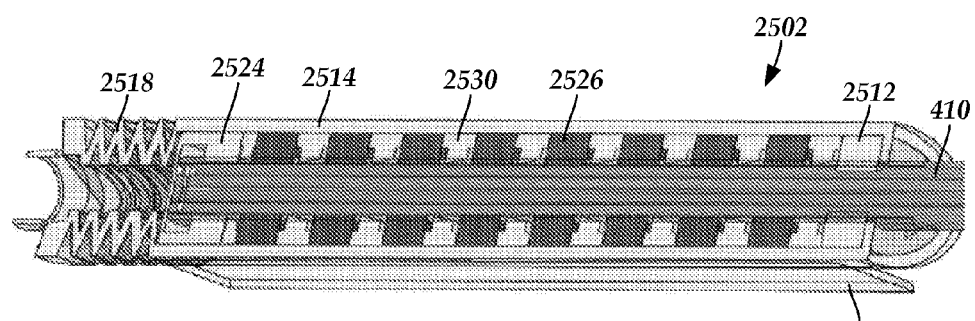
FIG. 25C is a schematic longitudinal cross-sectional view of one embodiment of a lead or lead extension inserted into the connector of FIG. 25A, according to the invention.

FIG. 25C is a schematic longitudinal cross-sectional view of one embodiment of the lead or lead extension 410 inserted into the connector 2502. In FIG. 25C, the lead 410 is fully inserted into the connector 2502 such that a proximal end of the lead or lead extension 410 is contacting the end stop 2524. In at least some embodiments, the spacing between adjacent connector contacts 2526 is equal to the spacing between adjacent terminals of the received lead or lead extension 410. In at least some embodiments, the connector contacts 2526 are spaced apart from one another such that when the lead or lead extension 410 is inserted into the port 2520 until a proximal end of the lead or lead extension 410 contacts the end stop 2524, the connector contacts 2526 align with at least some of the terminals of the received lead or lead extension 410.

In at least some embodiments, the connector 2502 additionally includes one or more conductor-carrying members 2540. In at least some embodiments, the conductor-carrying members 2540 provide one possible way to route conductors, such as conductive wires (not shown), from the connector contacts 2526 to the first end 2504 of the connector 2502. The conductor-carrying members 2540 may be formed from any substrate suitably sized and shaped for receiving conductors, such as conductive wires. It will be understood that conductors extending from connector contacts to the proximal end of the connector have been omitted from previous discussion and description, for clarity of illustration and discussion. Such conductors, however, may be present for each of the above-mentioned embodiments of the connectors. In at least some embodiments, the conductors extend to a proximal end of a lead extension. In other embodiments, the conductive wires extend to the electronic subassembly (3610 of FIG. 6) in a control module.

In at least some embodiments, the conductor are embedded in the one or more conductor-carrying members 2540. In at least some embodiments, the conductors are disposed in one or more lumens (not shown) extending though the one or more conductor-carrying members 2540. In at least some embodiments, the conductors extend from the one or more conductor-carrying members 2540 through lumens, such as the lumens 1202, in the strain relief arrangement 2518. In at least some embodiments, the one or more conductor-carrying members 2540 extend along a length of the connector housing 2514. In at least some embodiments, the one or more conductor-carrying members 2540 are coupled directly to the connector housing 2514. In at least some embodiments, the one or more conductor-carrying members 2540 are continuous with the connector housing 2514 such that the one or more conductor-carrying members 2540 form a portion of the connector housing 2514.

Figure 26:
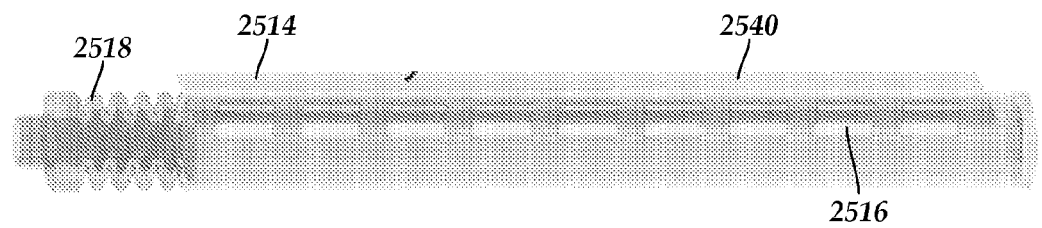
FIG. 26 is a schematic perspective view of one embodiment of a connector housing suitable for use with the connector of FIG. 25A, the connector housing including a tangential body for receiving conductors and defining an array of apertures for viewing within the connector housing, according to the invention.

FIG. 26 is a schematic perspective view of one embodiment of the connector housing 2514. In at least some embodiments, the connector housing 2514 is formed as a cover disposed over an array of coupleable members (e.g., connector contacts 2526 and spacers 2530). In at least some embodiments, individual coupleable members align (and couple together) with one another along the length 2508 within the connector housing 2514. In at least some embodiments, the array of coupleable members includes the retaining element 2512. In at least some embodiments, the array of coupleable members includes the end stop 2524.

Figure 27A:
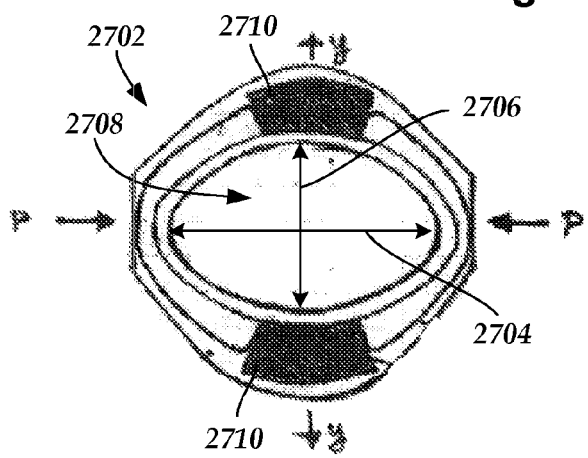
FIG. 27A is a schematic front view of one embodiment of an exemplary coupleable member with contacts, the coupleable member in a relaxed position such that a center aperture of the coupleable member is oval-shaped with a minor axis that is sized to prevent insertion of a lead or lead extension through the center aperture, according to the invention.

FIG. 27A is a schematic front view of one embodiment of an exemplary coupleable member 2702. The coupleable member 2702 has a major axis 2704, a minor axis 2706, and defines a port aperture 2708 that forms a portion of the port 2520 when aligned with other coupleable members 2702. In FIG. 27A, the coupleable member 2702 is shown in a relaxed position such that port aperture 2708 is oval-shaped. The port aperture 2708 is sized such that a diameter of the lead or lead extension 410 is smaller than the port aperture 2708 along the major axis 2706, yet larger that the port aperture 2708 along the minor axis 2706. Thus, the lead or lead extension 410 does not readily extend through the port aperture 2708 when the coupleable member 2702 is in the relaxed position.

Coupleable members 2702 can include one or more elements that enable the coupleable member to function as, for example, the end stop 2524, the connector conductors 2526, the spacers 2530, the retaining element 2512, or the like. In FIG. 27A, the coupleable member 2702 includes contacts 2710, thereby enabling the coupleable member 2702 to function as a connector contact. In at least some embodiments, various coupleable members 2702 have similar transverse shapes and sizes.

Figure 27B:
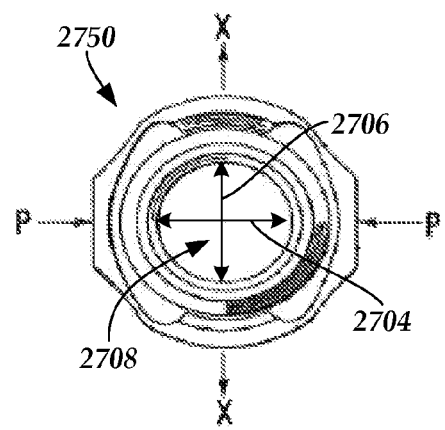
FIG. 27B is a schematic front view of one embodiment of an exemplary coupleable member in a flexed position such that a two opposing sides of a major axis of a center aperture are pressed inwardly, thereby expanding a minor axis of the center aperture to a diameter large enough to enable insertion of a lead or lead extension through the center aperture, according to the invention.

FIG. 27B is a schematic front view of the coupleable member 2750 in a flexed position, where one or more inwardly-directed forces (shown by the letter "P" in FIGS. 27A and 27B) are applied along the major axis 2704 of the coupleable member 2702. The one or more inwardly-directed forces cause the major axis 2704 to contract and the minor axis 2706 to expand. At some range of applied pressure, the minor axis 2706 expands enough to enable the lead or lead extension 410 to pass through the port aperture, while the major axis 2704 does not compress to a length that does not readily enable the lead or lead extension 410 to extend through the port aperture 2708. In at least some embodiments, once the application of the force(s) is ceased, the coupleable member 2702 transitions back to the relaxed position. It will be understood that, the each of the different types of coupleable members (e.g., the end stop 2524, the connector conductors 2526, the spacers 2530, and the retaining element 2512) can transition between a relaxed position and a flexed position.

Thus, in at least some embodiments, force may be applied to one or more ends of the major axes 2704 of the coupleable members disposed along the connector 2502 to decrease the width along the major axis 2704 and increase the width along the minor axis 2706, thereby enabling insertion of the lead or lead extension 410 into the connector 2502. Once the lead or lead extension 410 is inserted into the connector 2502, the force can be removed. Removal of the force causes the coupleable members to transition back to the original position and physically grasp and retain the inserted lead or lead extension 410. In at least some embodiments, when the lead or lead extension 410 is inserted into the connector 2502 formed from one or more coupleable members in relaxed positions, the lead or lead extension 410 is retained by the coupleable members via an interference fit between the lead or lead extension 410 and at the least the minor axis 2706 of the coupleable members.

In at least some embodiments, the interference fits of the mating elements are enough to sufficiently retain the lead or lead extension 410 in the connector 1502 without employing the retaining element 2512. In at least some embodiments, the connector 2502 includes the retaining element 2512 to ensure retention of the lead or lead extension 410.

Figure 28:
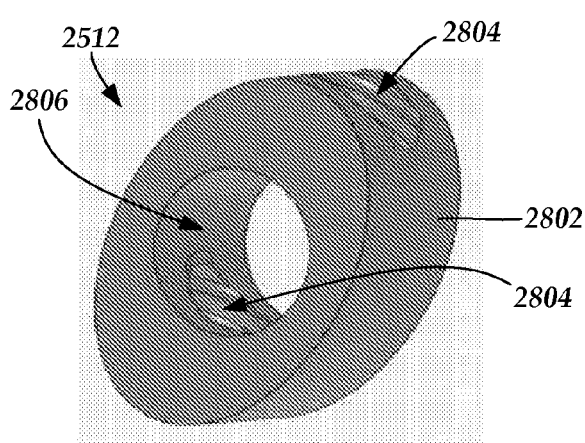
FIG. 28 is a schematic perspective view of another embodiment of a fastener block suitable for use in the retaining element of FIG. 14, according to the invention.

FIG. 28 is a schematic perspective view of another embodiment of the retaining element 2512 formed as a coupleable member. The retaining element 2512 includes a fastener block 2802 that defines one or more fastener receivers 2804 for receiving one or more fasteners, as described above with reference to the embodiment illustrated in FIG. 15. In at least some embodiments, the fastener block 2802 also defines a port aperture 2806 that forms a portion of the port 2520. In FIG. 28, two fastener receivers 2804 are shown on opposite ends of the fastener block 2802. Any number of fastener receivers 2804, however, can be disposed in the fastener block 2802 in any configuration.

Figure 29A:
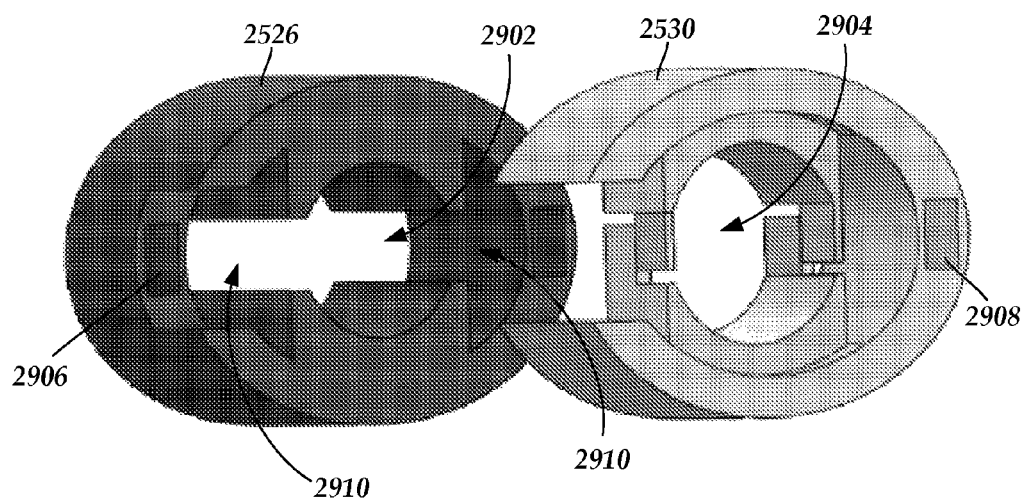
FIG. 29A is a schematic front perspective view of one embodiment of a coupleable member configured for receiving contacts and a coupleable member configured to function as a non-conductive spacer, according to the invention.

FIG. 29A is a schematic front perspective view of one embodiment of the connector contact 2526 and the spacer 2530, both of which are formed as coupleable members. The connector contact 2526 defines a port aperture 2902. The spacer 2530 also defines a port aperture 2904. In at least some embodiments, the connector contact 2526 defines one or more conductive wire ports 2906 for routing one or more conductive wires (not shown) from the connector contact 2526 to the first end 2504 of the connector 2502. In at least some embodiments, the spacer 2530 also defines one or more conductive wire ports 2908. Note that the connector contact 2526 shown in FIG. 29A does not show the contacts. The contacts may be formed from any conductive material suitable for implantation. In at least some embodiments, the contacts are sized and shaped for being disposed in one or more of the connector apertures 2910 of the connector contact 2526.

Figure 29B:
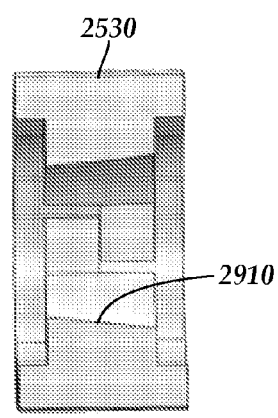
FIG. 29B is a schematic cross-sectional view of one embodiment of the coupleable member configured to function as a non-conductive spacer of FIG. 29A, according to the invention.

FIG. 29B is a schematic cross-sectional view of one embodiment of the spacer 2530. In at least some embodiments, the port aperture 2904 includes a sloped surface 2910 for contacting the lead or lead extension 410 when the lead or lead extension 410 is inserted into connector 2502. In at least some embodiments, at least a portion of the sloped surface 2910 extends into the port aperture 2904 more than corresponding surfaces of the port aperture 2904 of the connector contact 2526. It may be advantageous to form the port aperture 2904 with the sloped surface 2910 extending into the port aperture 2904 more than corresponding surfaces of the port aperture 2902 of the connector contact 2526 to increase electrical isolation between adjacent connector contacts 2526. It may be advantageous to form the spacer 2530 such that the sloped surface 2910 slopes inwardly from the second end 2506 to the first end 2504 so that, when the lead or lead extension 410 is inserted in the port aperture 2904, the lead or lead extension 410 compresses the sloped surface 2901 rather than curling up the sloped surface 2910.

Figure 30:
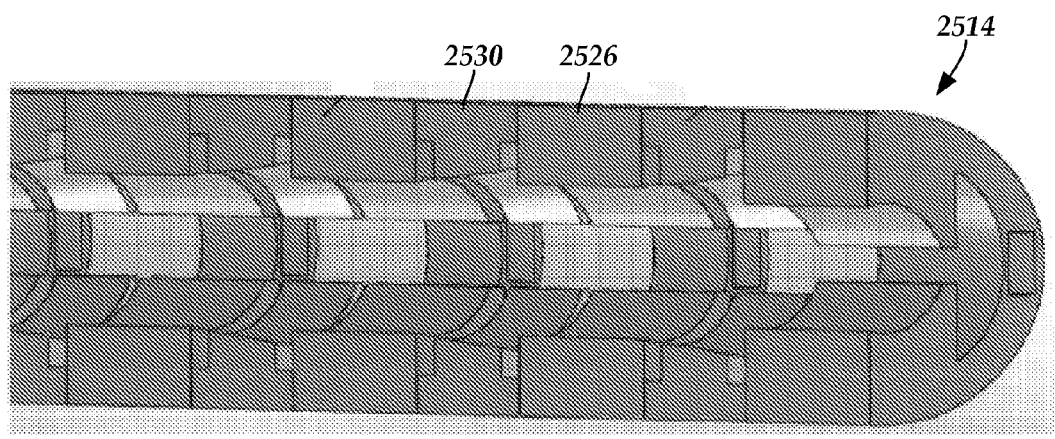
FIG. 30 is a schematic perspective longitudinal cross-sectional view of one embodiment of a plurality of axially-aligned coupleable members, the axially-aligned coupleable members including alternating coupleable members configured for receiving contacts and coupleable members configured to function as non-conductive spacers, according to the invention.

FIG. 30 is a schematic perspective longitudinal cross-sectional view of one embodiment of a portion of the connector housing 2514. In at least some embodiments, the connector housing 2514 includes an array of connector contacts 2526 formed as coupleable members, where each individual connector contact 2526 is separated from one or more adjacent connector contacts 2526 by at least one spacer 2530, also formed as a coupleable member.

Figure 31:
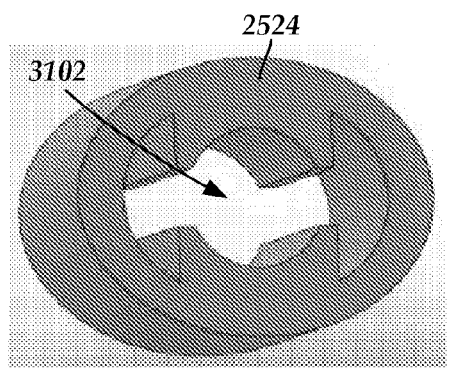
FIG. 31 is a schematic front perspective view of one embodiment of a coupleable member configured to function as an end stop of FIG. 25B, according to the invention.

FIG. 31 is a schematic front perspective view of one embodiment of the end stop 2524 formed as a coupleable member. The end stop 2524 defines a port aperture 3102. In at least some embodiments, the end stop 2524 includes a retaining surface (e.g., a wall, netting, mesh, strips, or the like) of material that prevents the lead or lead extension 410 from sliding axially beyond the end stop 2524 when the lead or lead extension 410 is disposed in the connector 2502. In at least some embodiments, the end stop 2524 forms an interference fit with the lead or lead extension 410 that prevents the lead or lead extension 410 from sliding axially beyond the end stop 2524 when the lead or lead extension 410 is disposed in the connector 2502.

Figure 32:
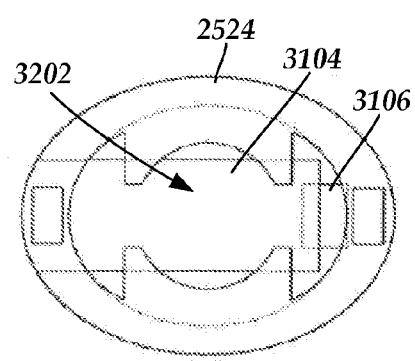
FIG. 32 is a schematic front view of one embodiment of the coupleable member configured to function as an end stop of FIG. 25B, the end stop including a feedback mechanism, according to the invention.

In at least some embodiments, the end stop 2524 includes a feedback mechanism. FIG. 32 is a schematic front view of one embodiment of the end stop 2524 including a feedback mechanism 3202. The feedback mechanism 3202 includes a first tab 3104 and a second tab 3106. In at least some embodiments, the feedback mechanism 3202 is formed in a manner similar to the feedback mechanism 1002 discussed above, with reference to FIGS. 10A-10D. In at least some embodiments, the feedback mechanism 3202 operates in a manner similar to the feedback mechanism 1002 discussed above, with reference to FIGS. 10A-10D.

Figure 33:
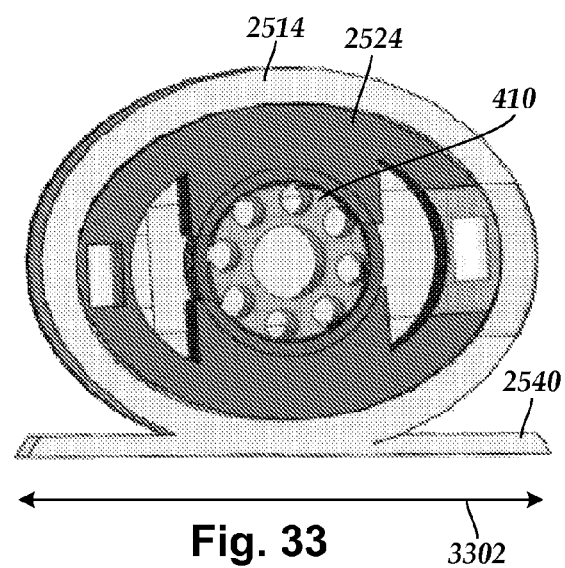
FIG. 33 is a schematic transverse cross-sectional view of one embodiment of a portion of the lead or lead extension of FIG. 4A inserted into the end stop of FIG. 25B which, in turn is inserted into the connector housing of FIG. 25A, according to the invention.

FIG. 33 is a schematic transverse cross-sectional view of one embodiment of a transverse slice of the lead or lead extension 410 disposed in a transverse slice of the connector housing 2514. The lead or lead extension 410 is disposed in the end stop 2524, which is formed as a coupleable member, and which is disposed in the connector housing 2514. FIG. 33 also shows the conductor-carrying member 2540 coupled tangentially to the connector housing 2514. In at least some embodiments, the conductor-carrying member 2540 has a width 3302 no larger than a corresponding transverse diameter of the connector housing 2514. In at least some embodiments, the conductor-carrying member 2540 couples to the connector housing 2514 such that the conductor-carrying member 2540 does not increase a diameter of the connector housing 2514.

Figure 34:
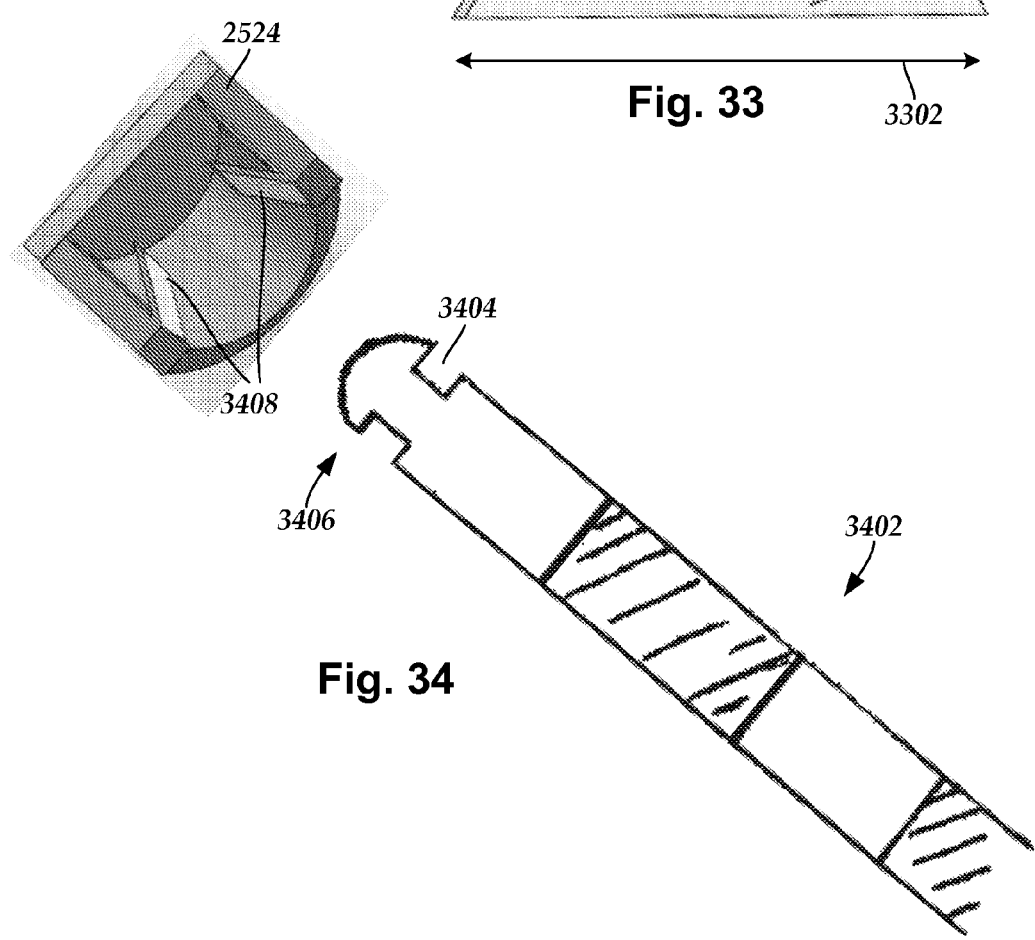
FIG. 34 is a schematic side view of one embodiment of a lead or lead extension configured and arranged for insertion into a perspective, longitudinal cross-sectional view of one embodiment of a coupleable member configured to function as an end stop with a feedback mechanism, according to the invention.

Turning now to FIG. 34, in at least some embodiments, the end stop 2524 is formed as a coupleable member that includes a locking mechanism for retaining a lead or lead extension in the connector. In at least some embodiments, the locking mechanism retains the lead or lead extension in the connector such that terminals of the lead or lead extension align with connector contacts disposed in the connector.

FIG. 34 is a schematic side view of one embodiment of a lead or lead extension 3402 configured and arranged for insertion into a perspective, longitudinal cross-sectional view of one embodiment of the end stop 2524 formed as a coupleable member. The lead or lead extension 3402 includes one or more features 3404 in proximity to a proximal end 3406. The end stop 2524 includes one or more retention mechanisms, such as angled tabs 3408. In at least some embodiments, when the lead or lead extension 3402 is inserted into the connector 2502 the proximal end 3406 of the lead or lead extension 3402 engages the one or more angled tabs 3408 such that the one or more angled tabs 3408 retain the lead or lead extension 3402. In at least some embodiments, the one or more angled tabs 3408 engage the lead or lead extension 3402 via the one or more features 3404.

In at least some embodiments, the one or more features 3404 include one or more grooves, reduced-diameter regions, protrusions, or the like. In at least some embodiments, the lead or lead extension 3402 can be released from the one or more angled tabs 3408. In at least some embodiments, the lead or lead extension 3402 can be released from the one or more angled tabs 3408 by squeezing the end stop 2524 along an axis that is perpendicular to an axis of the one or more angled tabs 3408.

Figure 35:
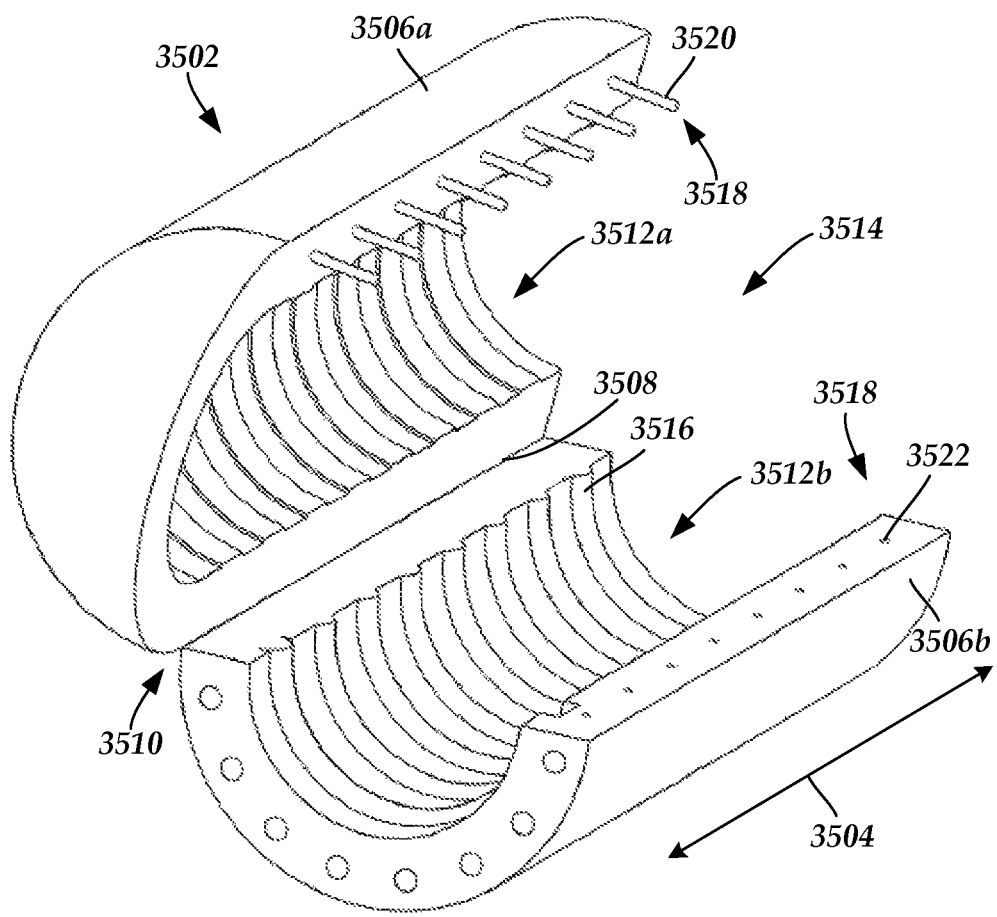
FIG. 35 is a perspective view of another embodiment of a connector with a hinged opening along a longitudinal axis of the connector, according to the invention.

FIG. 35 is a perspective view of another embodiment of a connector 3502 that opens along one or more hinges 3508 extending along a fulcrum 3510. In at least some embodiments, two body portions 3506a and 3506b are coupled together by the one or more hinges 3508 extending along the fulcrum 3510. The body portions 3506a, 3506b each include pockets 3512a and 2512b, respectively, that collectively provide a housing 3514 for receiving the lead or lead extension 410. Connector contacts 3516 are disposed in one or more of the pockets 3512a, 3512b in an arrangement configured and arranged to align with terminals of the inserted lead or lead extension 410 when the lead or lead extension 410 is inserted into the connector 3502.

In at least some embodiments, the connector 3502 includes a locking mechanism 3518 for retaining the lead or lead extension 410 within the connector 3502. In at least some embodiments, the locking mechanism 3518 includes one or more pins 3520 disposed on either of the body portions 3506a, 3506b and retaining apertures 3522 that are disposed on the other of the body portions 3506a, 3506b and that are configured and arranged to receive the one or more pins 3520 when the body portions 3506a, 3506b are closed. In at least some embodiments, the one or more retaining apertures 3522 receive the one or more pins 3520 in a spring-like manner where the pins 3520 can be clicked into the apertures 3522 and clicked out of the apertures 3522, thereby providing a feedback mechanism to a medical practitioner.

In at least some embodiments, one or more of the connectors, 402, 1502, and 2502 are disposed on lead extensions, as shown in FIG. 3B. In at least some embodiments, one or more of the connectors, 402, 1502, and 2502 can be disposed on devices other than lead extensions, such as on a control module, a splitter, an adapter, or the like.

Figure 6:
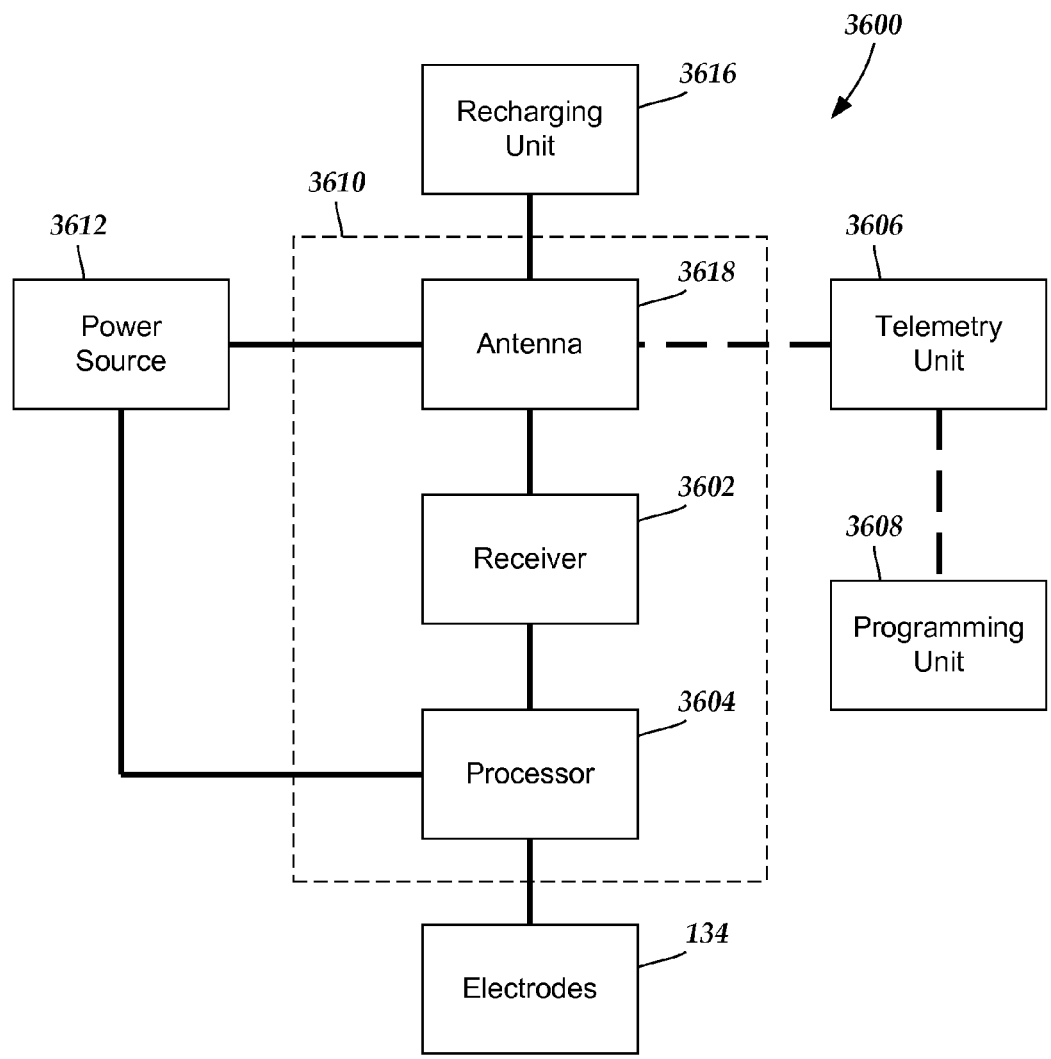
FIG. 6 is a schematic overview of one embodiment of components of a stimulation system, including an electronic subassembly disposed within a control module, according to the invention.

FIG. 6 is a schematic overview of one embodiment of components of an electrical stimulation system 3600 including an electronic subassembly 3610 disposed within a control module. It will be understood that the electrical stimulation system can include more, fewer, or different components and can have a variety of different configurations including those configurations disclosed in the stimulator references cited herein.

Some of the components (for example, power source 3612, antenna 3618, receiver 3602, and processor 3604) of the electrical stimulation system can be positioned on one or more circuit boards or similar carriers within a sealed housing of an implantable pulse generator, if desired. Any power source 3612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 3618 or a secondary antenna. The external power source can be in a device that is mounted on the skin of the user or in a unit that is provided near the user on a permanent or periodic basis.

If the power source 3612 is a rechargeable battery, the battery may be recharged using the optional antenna 3618, if desired. Power can be provided to the battery for recharging by inductively coupling the battery through the antenna to a recharging unit 3616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 3604 is generally included to control the timing and electrical characteristics of the electrical stimulation system. For example, the processor 3604 can, if desired, control one or more of the timing, frequency, strength, duration, and waveform of the pulses. In addition, the processor 3604 can select which electrodes can be used to provide stimulation, if desired. In some embodiments, the processor 3604 may select which electrode(s) are cathodes and which electrode(s) are anodes. In some embodiments, the processor 3604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 3608 that, for example, allows modification of pulse characteristics. In the illustrated embodiment, the processor 3604 is coupled to a receiver 3602 which, in turn, is coupled to the optional antenna 3618. This allows the processor 3604 to receive instructions from an external source to, for example, direct the pulse characteristics and the selection of electrodes, if desired.

In one embodiment, the antenna 3618 is capable of receiving signals (e.g., RF signals) from an external telemetry unit 3606 which is programmed by a programming unit 3608. The programming unit 3608 can be external to, or part of, the telemetry unit 3606. The telemetry unit 3606 can be a device that is worn on the skin of the user or can be carried by the user and can have a form similar to a pager, cellular phone, or remote control, if desired. As another alternative, the telemetry unit 3606 may not be worn or carried by the user but may only be available at a home station or at a clinician's office. The programming unit 3608 can be any unit that can provide information to the telemetry unit 3606 for transmission to the electrical stimulation system 3600. The programming unit 3608 can be part of the telemetry unit 3606 or can provide signals or information to the telemetry unit 3606 via a wireless or wired connection. One example of a suitable programming unit is a computer operated by the user or clinician to send signals to the telemetry unit 3606.

The signals sent to the processor 3604 via the antenna 3618 and receiver 3602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 3600 to cease operation, to start operation, to start charging the battery, or to stop charging the battery. In other embodiments, the stimulation system does not include an antenna 3618 or receiver 3602 and the processor 3604 operates as programmed.

Optionally, the electrical stimulation system 3600 may include a transmitter (not shown) coupled to the processor 3604 and the antenna 3618 for transmitting signals back to the telemetry unit 3606 or another unit capable of receiving the signals. For example, the electrical stimulation system 3600 may transmit signals indicating whether the electrical stimulation system 3600 is operating properly or not or indicating when the battery needs to be charged or the level of charge remaining in the battery. The processor 3604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an implantable medical device, the connector comprising:
   an elongated connector housing having a first end, a second end, a length, and an outer surface, the connector housing defining a port at the second end of the connector housing that extends along at least a portion of the length of the connector housing, the port configured and arranged for receiving a proximal end of a lead or lead extension,
   a plurality of connector contacts disposed in the connector housing, the connector contacts configured and arranged for coupling to terminals disposed on the proximal end of the lead or lead extension when the proximal end of the lead or lead extension is received by the port; and
   a retaining element configured and arranged for retaining the lead or lead extension when the lead or lead extension is received by the port, wherein the retaining element comprises a conical collar disposed at the second end of the connector and a plurality of jaws at least partially disposed within the collar, wherein the collar and the plurality of jaws are configured and arranged to operate as a pin vice such that rotation of the collar about an axis aligned with the length of the connector causes the plurality of jaws to engage and tighten against an outer surface of the lead or lead extension when the lead or lead extension is received by the port.

2. The connector of claim 1, further comprising a plurality of contact housings abutting the port, wherein at least one of the plurality of connector contacts is disposed in each of the plurality of contact housings.

3. The connector of claim 2, wherein at least one of the plurality of connector contacts is disposed in one of the plurality of the contact housings such that the at least one of the plurality of connector contacts is positioned diagonally with respect to the length of the connector housing.

4. The connector of claim 1, wherein at least one of the plurality of connector contacts has an oval-shaped cross-section.

5. An electrical stimulating system comprising:
   a lead comprising
      a lead body with a proximal end, a distal end, and a longitudinal length,
      a plurality of electrodes disposed on the distal end of the lead,
      a plurality of terminals disposed on the proximal end of the lead, wherein at least one spacer is disposed between adjacent terminals of the plurality of electrodes, and
      a plurality of conductors, each conductor electrically coupling at least one of the electrodes to at least one of the terminals;
   a control module electrically coupled to the plurality of electrodes, the control module comprising
      a housing, and
      an electronic subassembly disposed in the housing;
   a lead extension having a proximal end and a distal end, wherein the proximal end of the lead extension is coupleable with the control module; and
   the connector of claim 1 coupled to the distal end of the lead extension;
   wherein the proximal end of the lead is configured and arranged for insertion into the port of the connector.

6. The electrical stimulating system of claim 5, further comprising an additional lead extension having a distal end and a proximal end, wherein the distal end of the additional lead extension is configured and arranged to receive the proximal end of the lead, and wherein the proximal end of the additional lead extension is configured and arranged for insertion into the port of the connector.

7. A lead extension for an implantable medical device, the lead extension comprising:
   a lead extension body having a proximal end and a distal end:
   a plurality of terminals disposed at the proximal end of the lead extension body;
   the connector of claim 1; and
   a plurality of conductors, each conductor electrically coupling at least one of the plurality of connector contacts of the connector to at least one of the terminals.

8. The lead extension of claim 7, wherein the connector housing further comprises at least one strain relief arrangement, the at least one strain relief arrangement configured and arranged to expand and contract along the length of the connector housing to absorb strain placed on the connector.

9. The lead extension of claim 7, further comprising an end stop disposed at a far end of the port, the end stop comprising a feedback mechanism for providing audible feedback to a user when the proximal end of the lead or lead extension is fully inserted into the port and the proximal end of the lead or lead extension contacts the end stop.

* * * * *